(12) United States Patent
Lui et al.

(10) Patent No.: US 8,945,536 B2
(45) Date of Patent: Feb. 3, 2015

(54) STEM CELL SHEET FOR TISSUE REPAIR

(75) Inventors: Po Yee Pauline Lui, Hong Kong (CN); Ming Ni, Beijing (CN); Yunfeng Rui, Nanjing (CN)

(73) Assignee: The Chinese University of Hong Kong, Hong Kong (CN)

( * ) Notice: Subject to any disclaimer, the term of this patent is extended or adjusted under 35 U.S.C. 154(b) by 300 days.

(21) Appl. No.: 13/355,055

(22) Filed: Jan. 20, 2012

(65) Prior Publication Data

US 2012/0189587 A1    Jul. 26, 2012

Related U.S. Application Data

(60) Provisional application No. 61/436,505, filed on Jan. 26, 2011.

(51) Int. Cl.
    *A61K 35/32*      (2006.01)
    *A61L 27/38*      (2006.01)

(52) U.S. Cl.
    CPC .......... *A61L 27/3895* (2013.01); *A61L 27/3834* (2013.01)
    USPC ........ 424/93.7; 623/13.11; 424/443; 424/422

(58) Field of Classification Search
    CPC .... A61K 35/32; A61K 35/28; A61L 27/2662; A61F 2/08
    See application file for complete search history.

(56) References Cited

U.S. PATENT DOCUMENTS

2006/0153815 A1    7/2006    Seyda et al.

FOREIGN PATENT DOCUMENTS

WO    WO 2006/110110    * 10/2006  ............. A61L 27/38
WO         2008/035843 A1    3/2008

OTHER PUBLICATIONS

Lee et al, "Fibroblastic Differnetiation of Human Mesenchymal Stem Cells Using Connective Tissue Growth Factor" Proceedings fo the 28th IEEE EMBS Annual International Conference. New York City, USA, Aug. 30-Sep. 3, 2006; pp. 775-778.*
Miyahara et al, "Monolayered mesenchymal stem cells repair scarred myocardium after myocardial infarction" Nature Medicine, 2006, vol. 12, No. 4, pp. 459-465.*
Bi et al., "Identification of tendon stem/progenitor cells and the role of the extracellular matrix in their niche," *Nature Medicine* 13(10):1219-27, Oct. 2007.

* cited by examiner

*Primary Examiner* — Allison Fox
(74) *Attorney, Agent, or Firm* — Seed IP Law Group PLLC

(57) ABSTRACT

Disclosed is a cell sheet for tissue repair and bio-artificial tissue engineering. The cell sheet comprises treated stem cell embedded in its self-secreted extracellular matrix (ECM) and formed a cell sheet. The cell sheet is formed by isolating the stem cell, expanding the stem cell and treating the stem cell with biological factors or factors leading to the production of biological factors, to induce its differentiation, production of extracellular matrix and formation of a cell sheet in vitro. The cell sheet is used as a bioactive material or as an acellular material for the promotion of tissue repairs or used to form a bio-artificial organ for tissue replacement. The cell sheet of the present invention eliminates the need to use scaffolds for cell delivery. The cell sheet facilitates in vivo cell transplantation and provides some tensile mechanical strength for bearing early mechanical load during tissue repair.

19 Claims, 41 Drawing Sheets

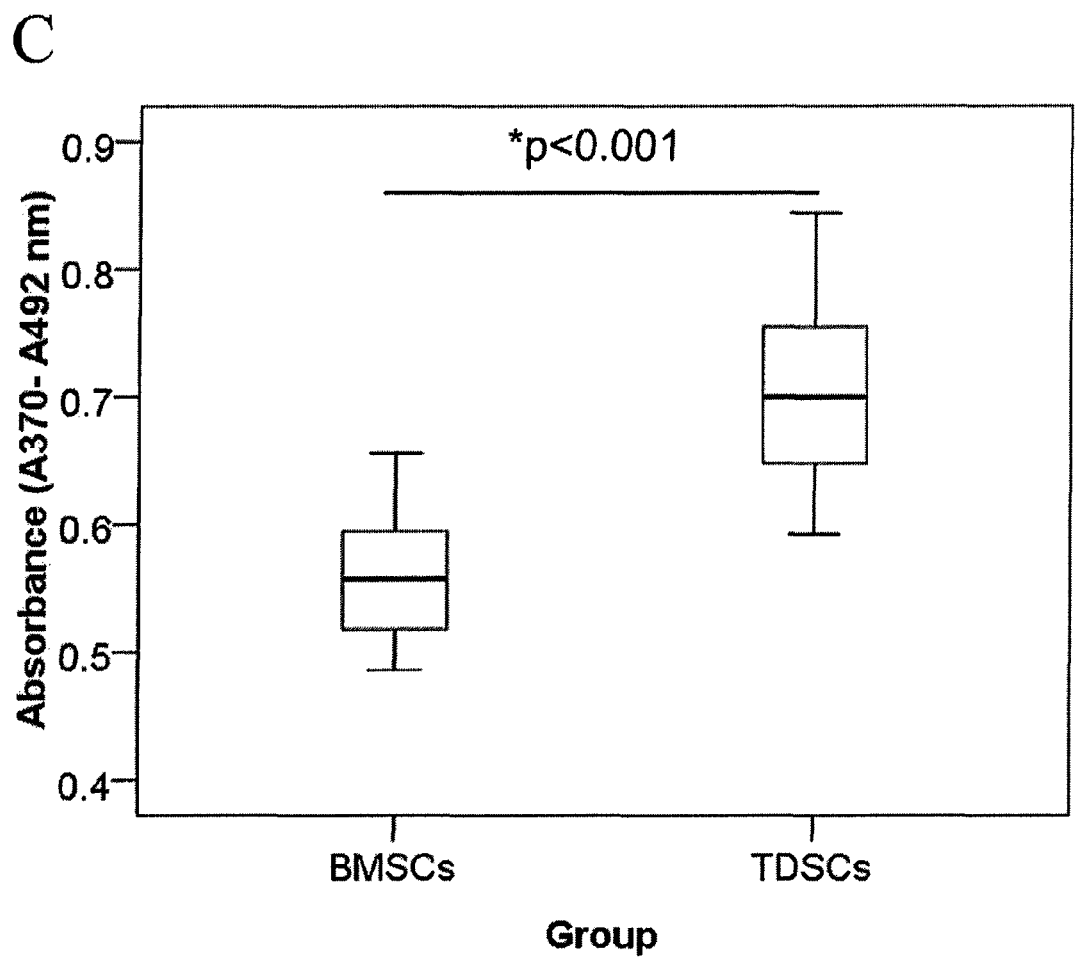
Figure 1 (continue)

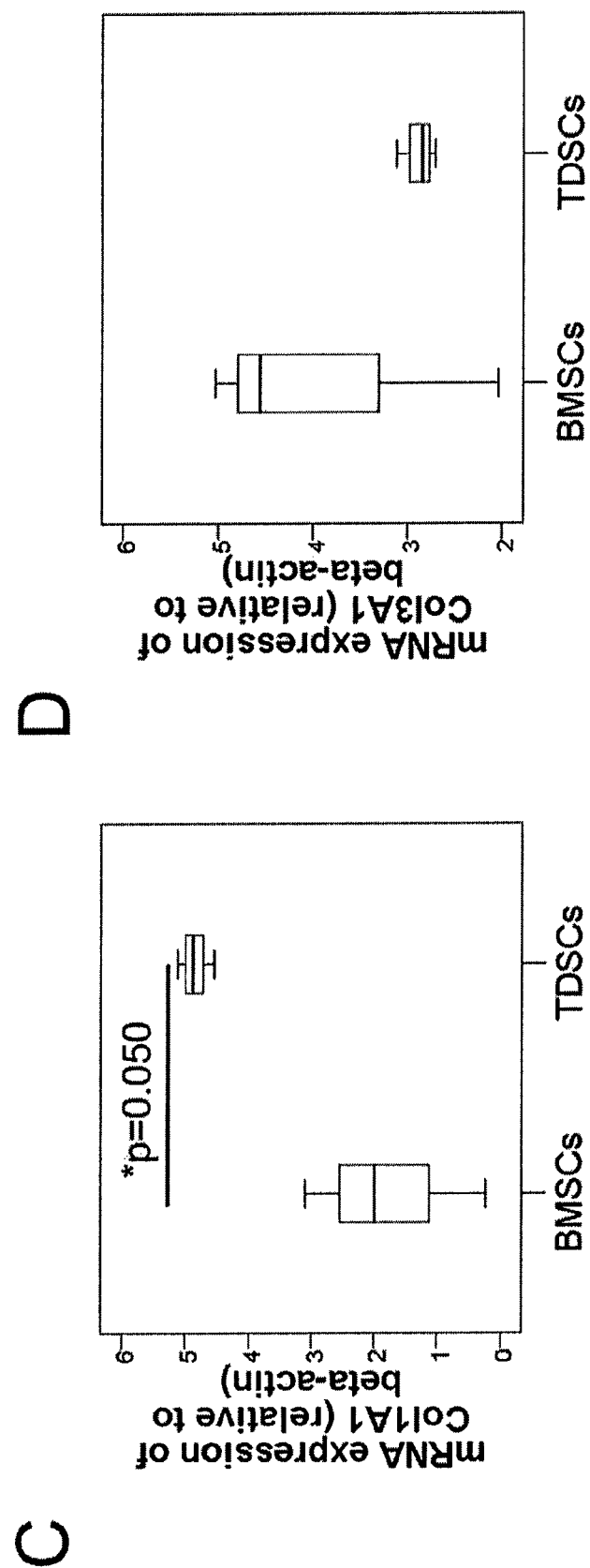
Figure 2 (continue)

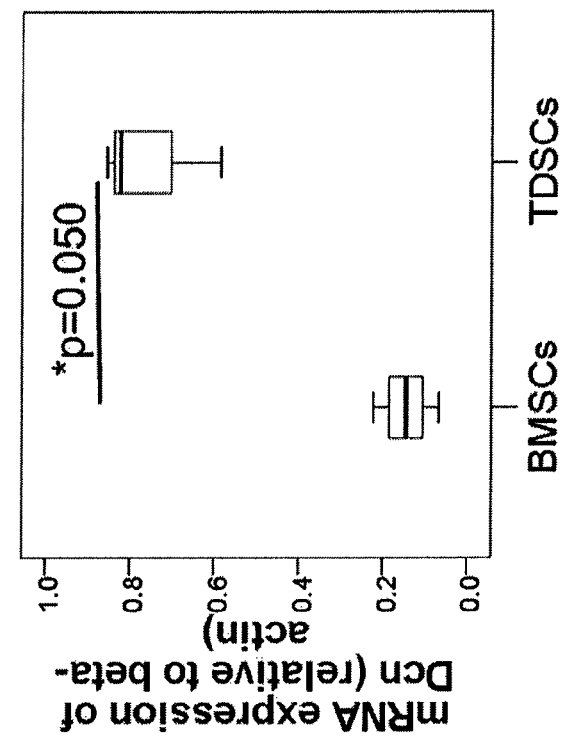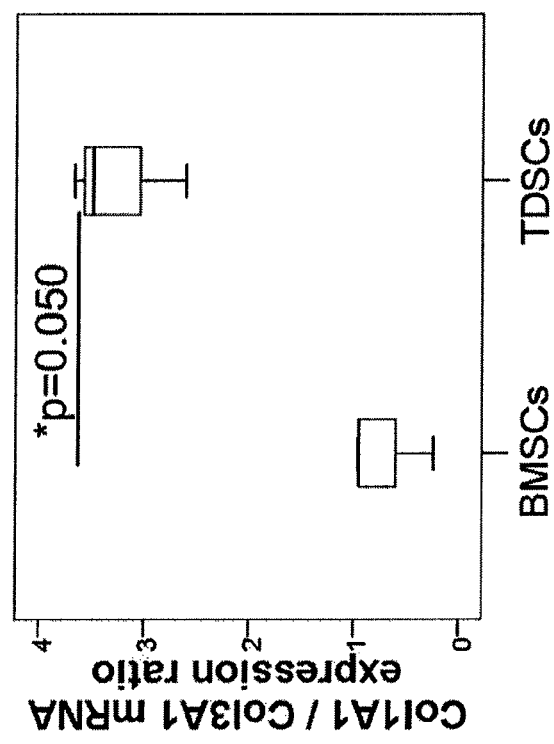
Figure 2 (continue)

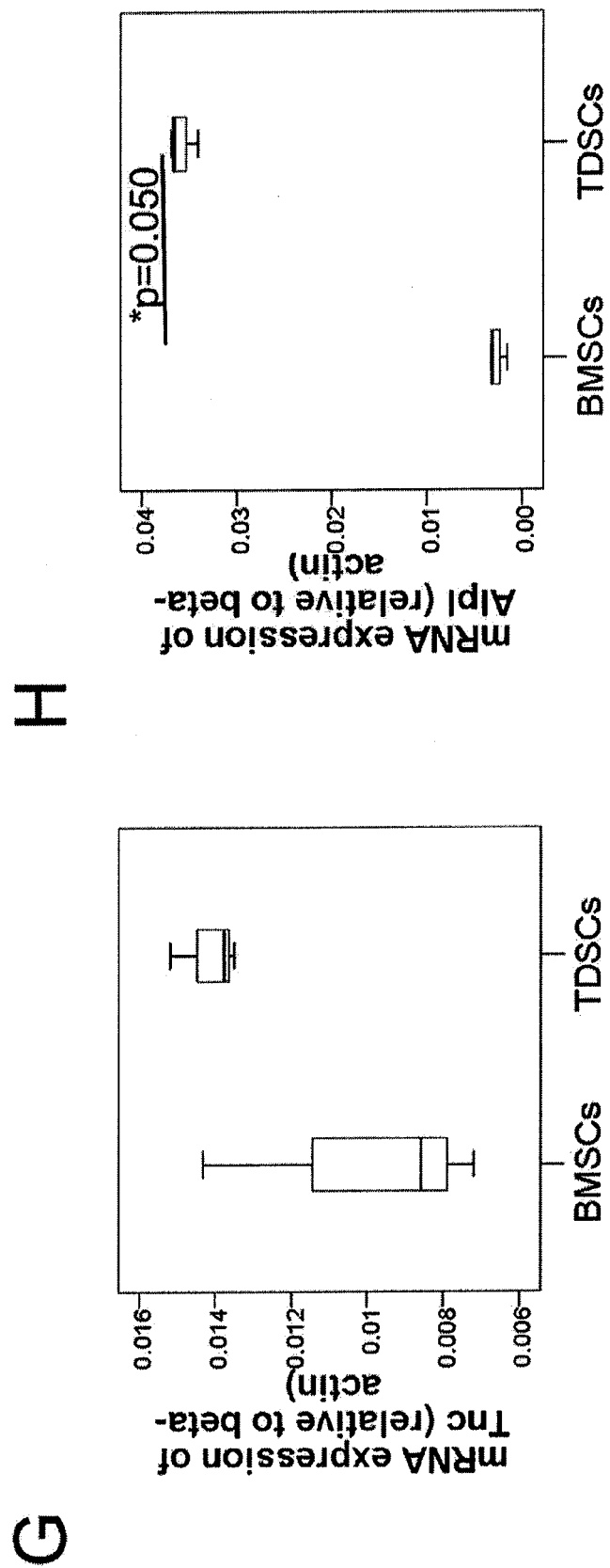
Figure 2 (continue)

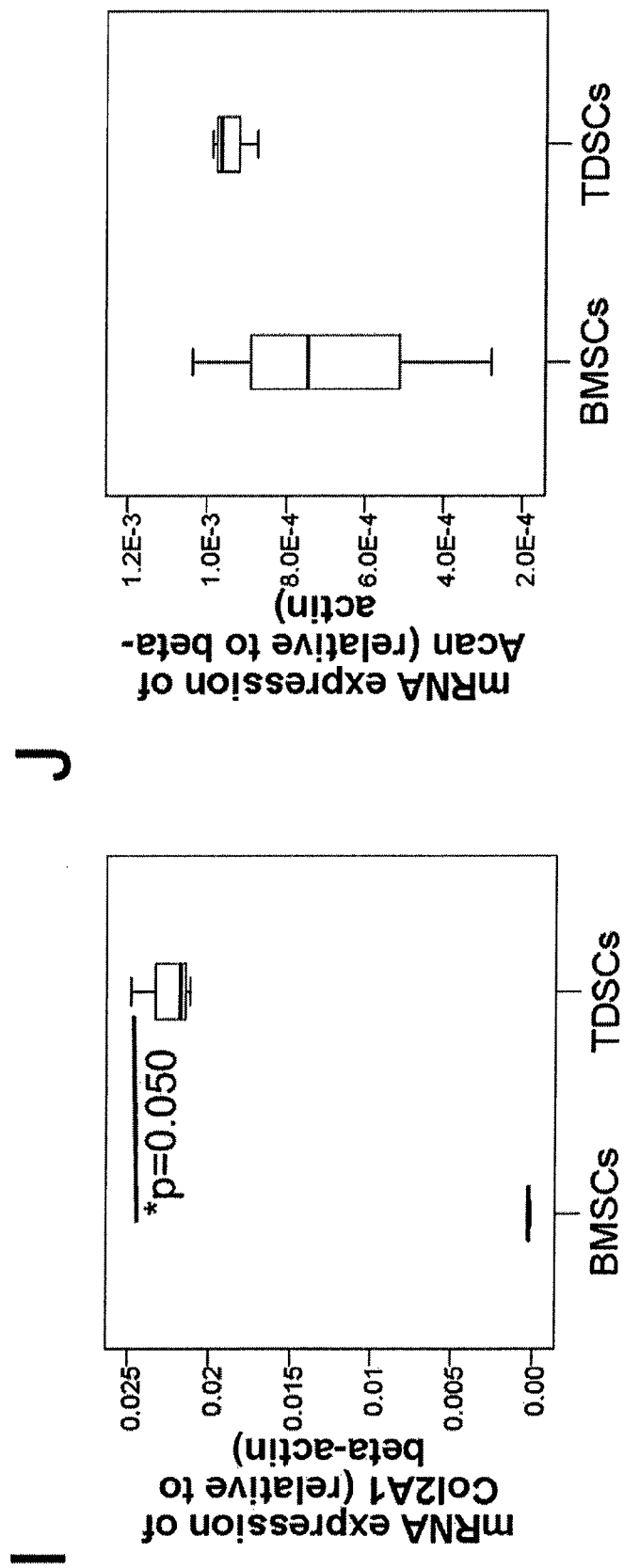
Figure 2 (continue)

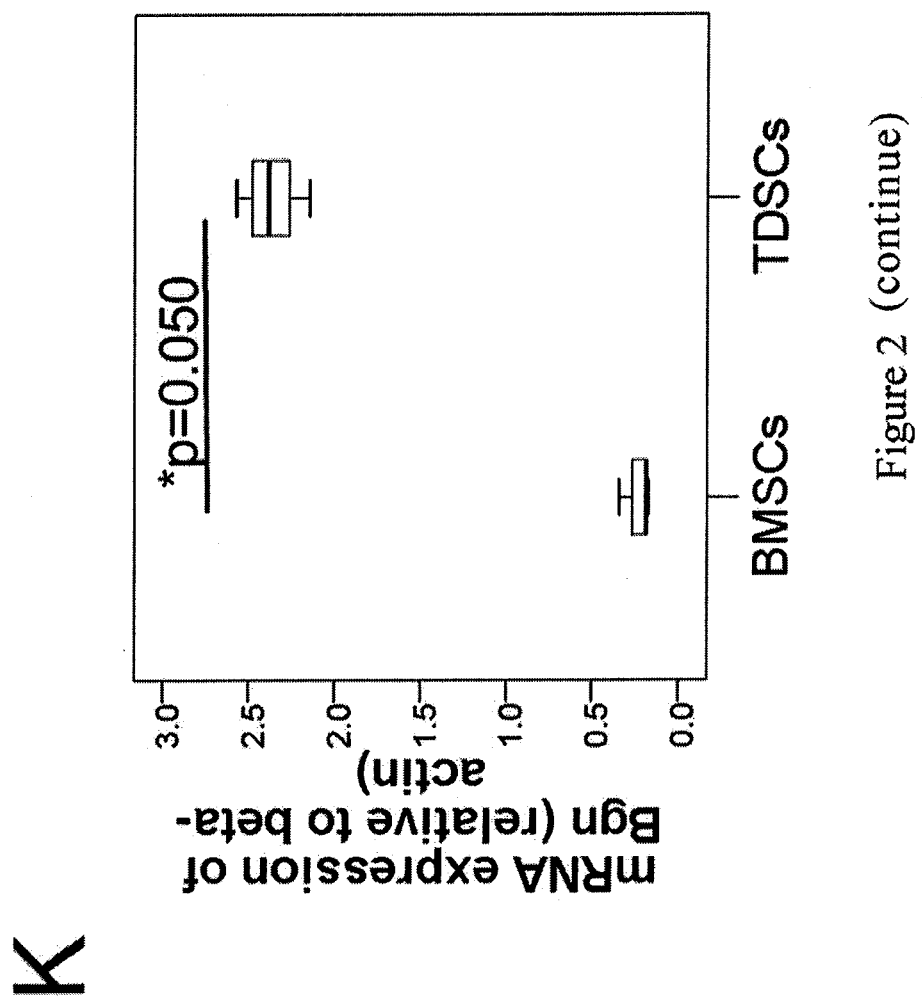
Figure 2 (continue)

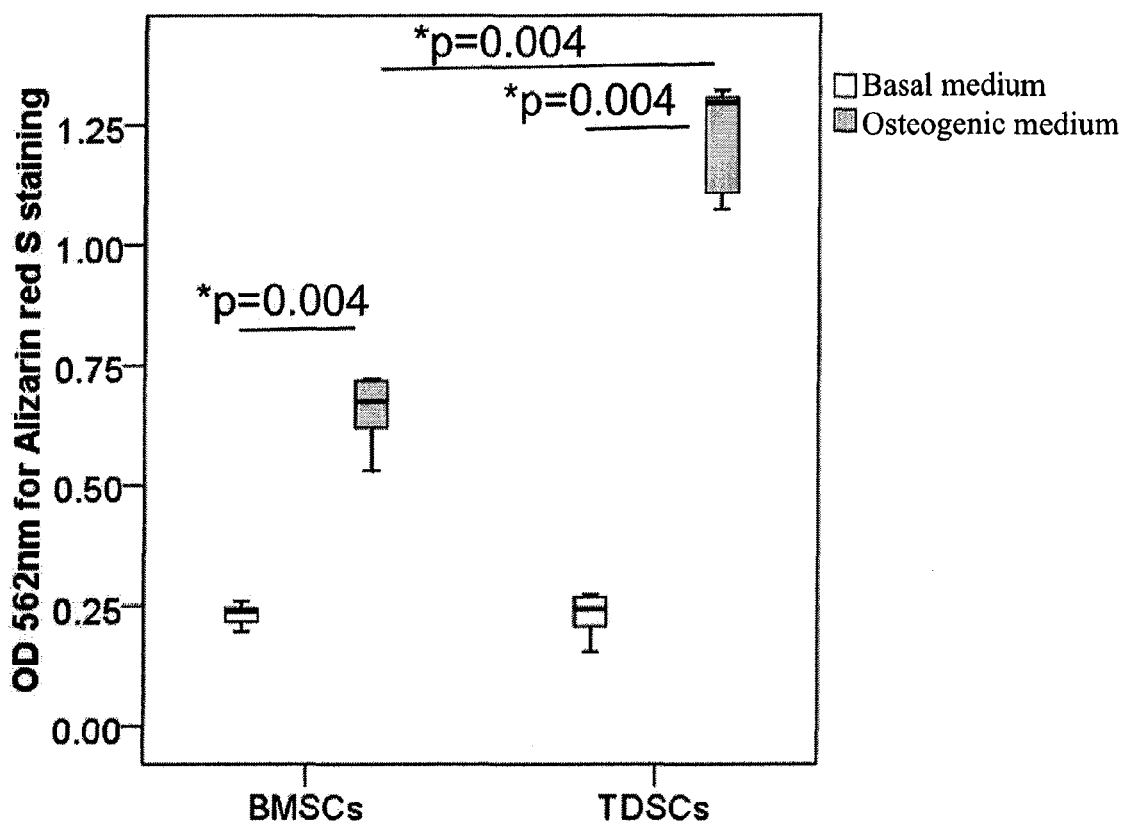
Figure 3 (continue)

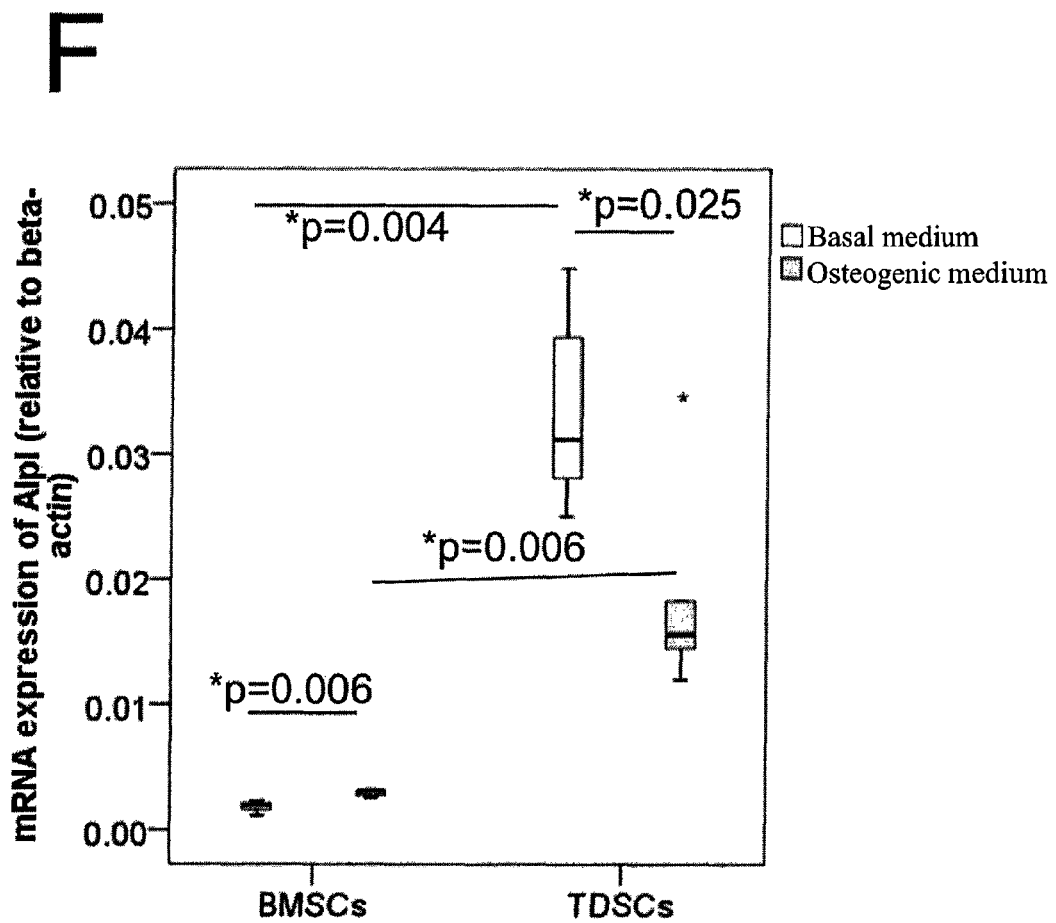
Figure 3 (continue)

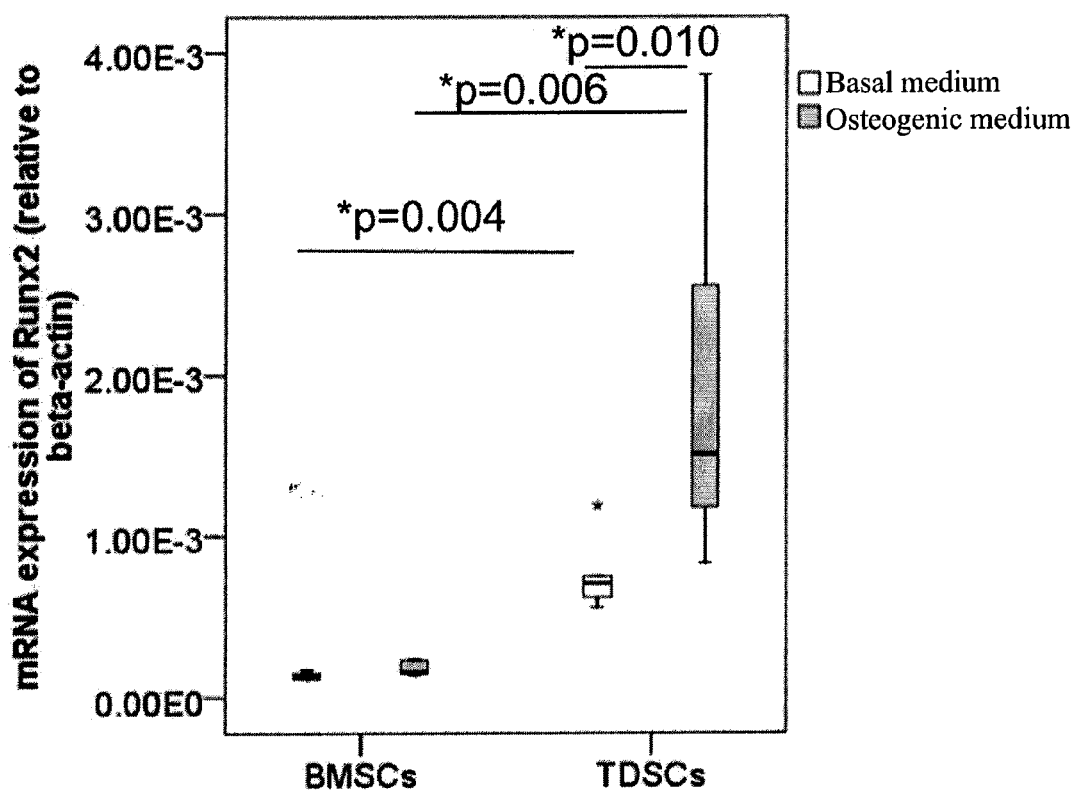
Figure 3 (continue)

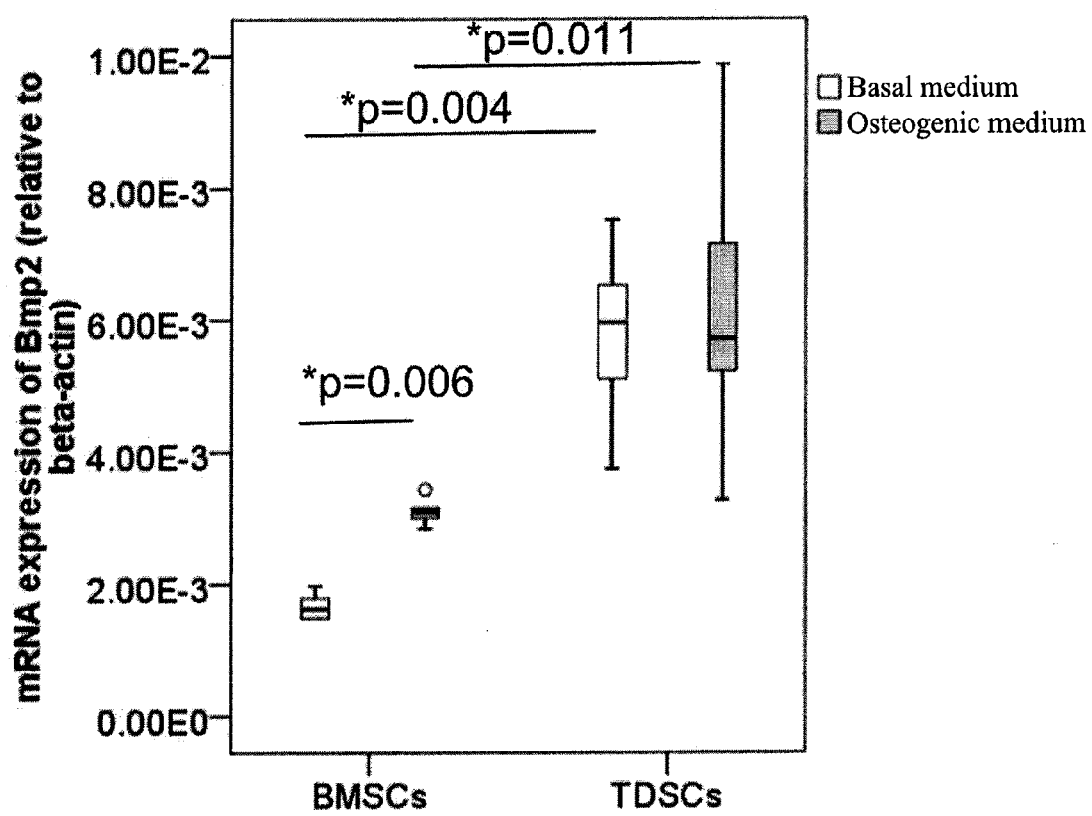
Figure 3 (continue)

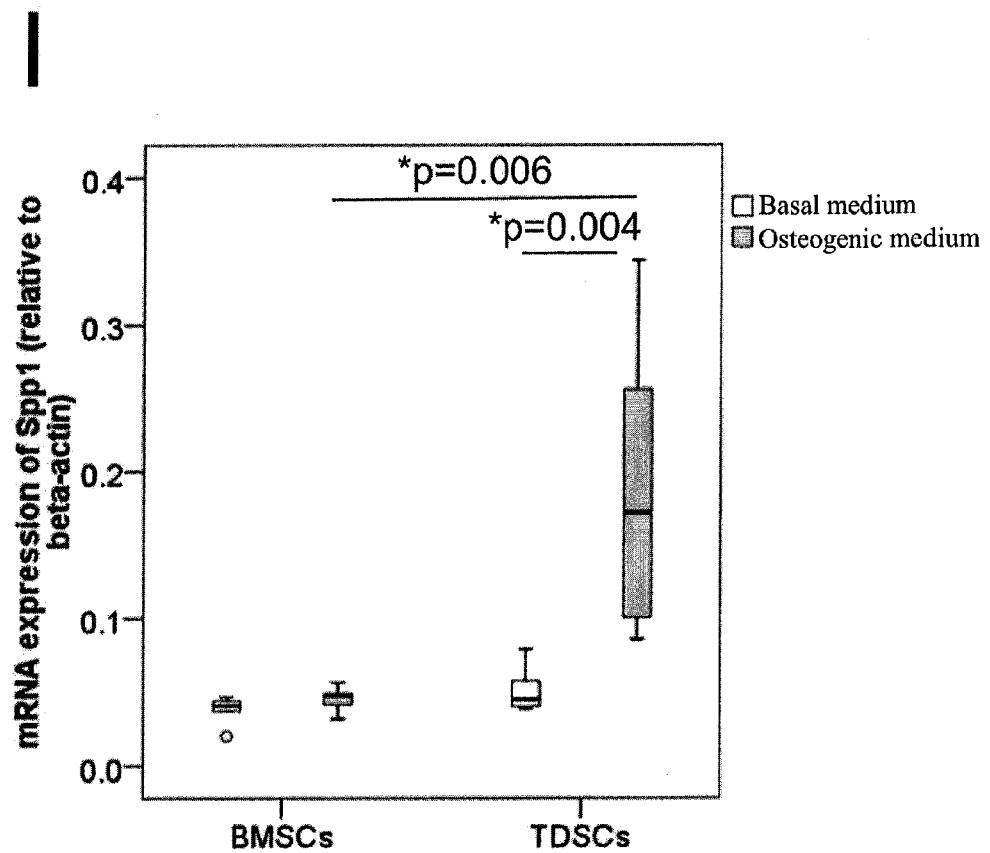
Figure 3 (continue)

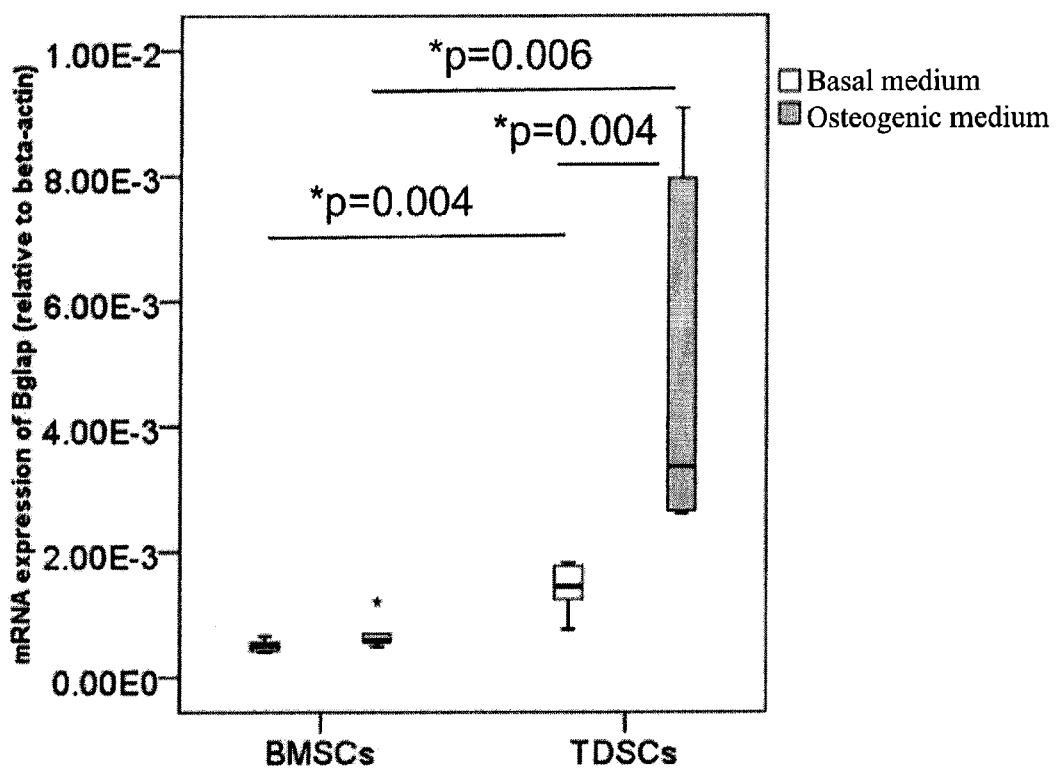
Figure 3 (continue)

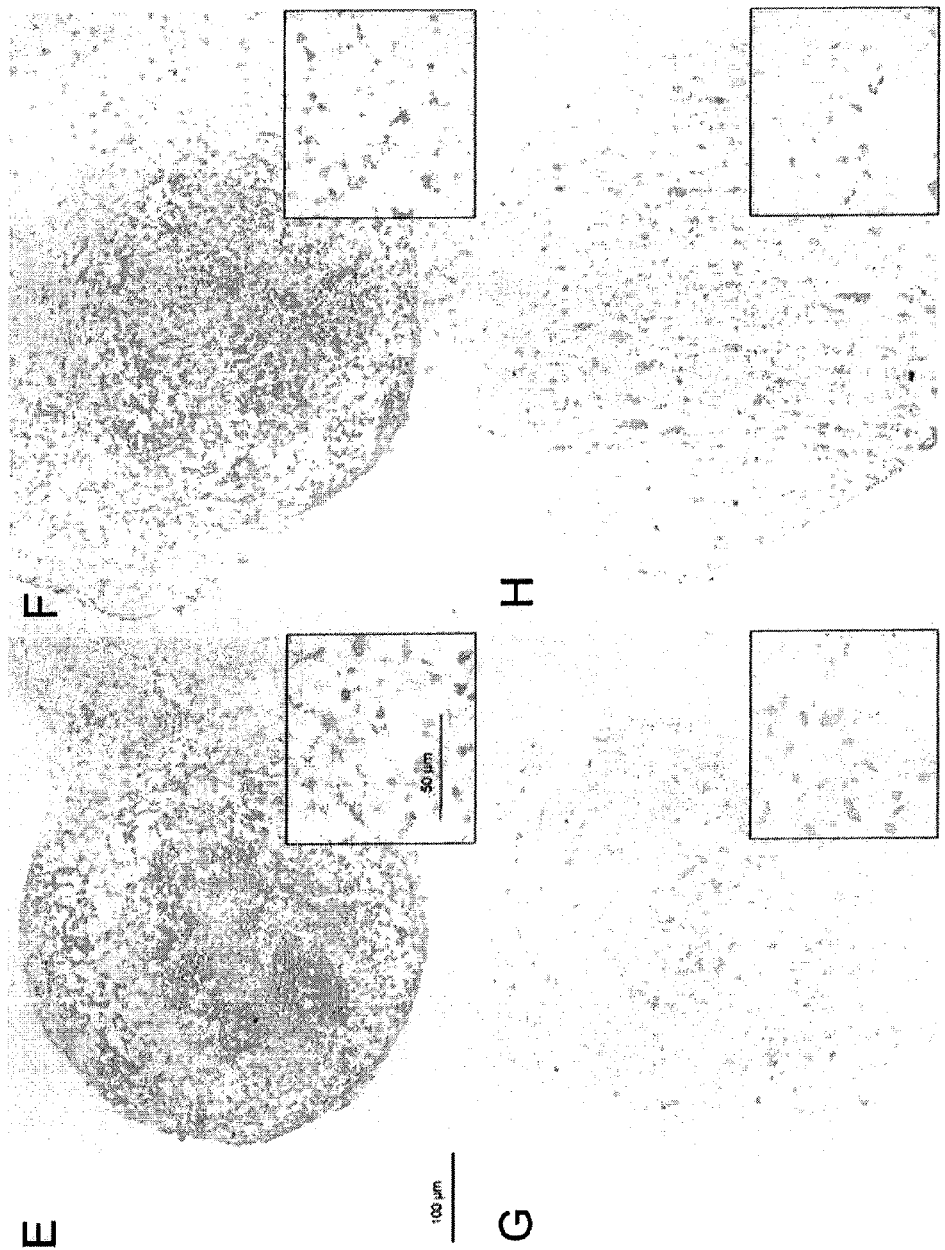
Figure 4 (continue)

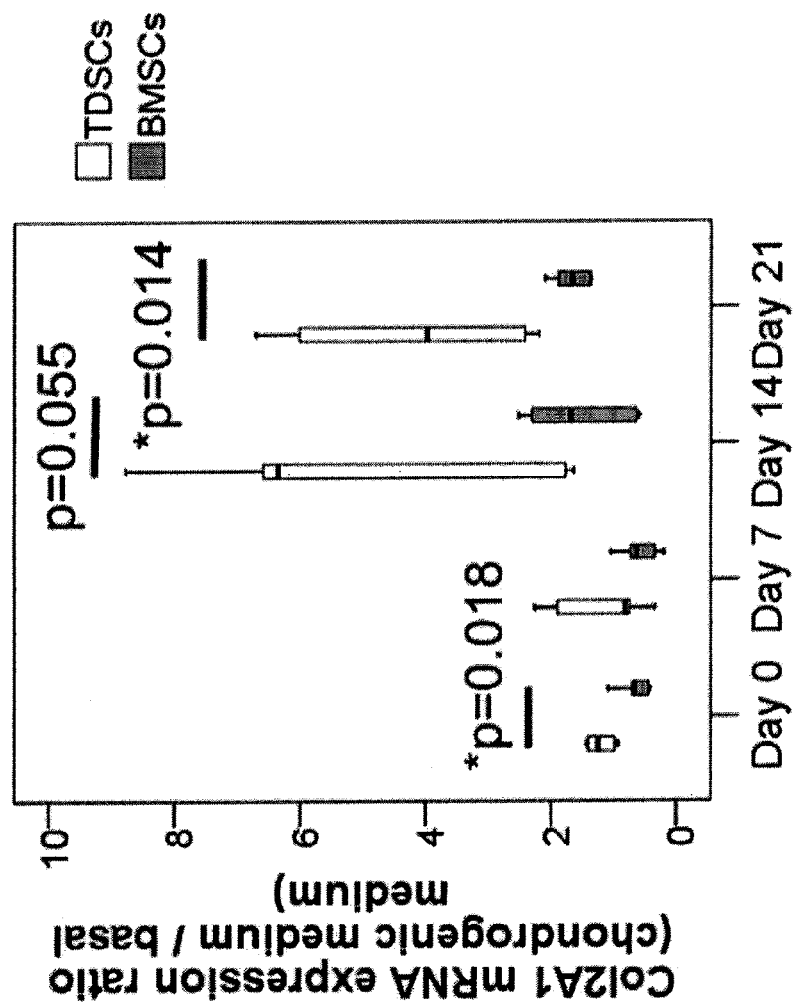
Figure 4 (continue)

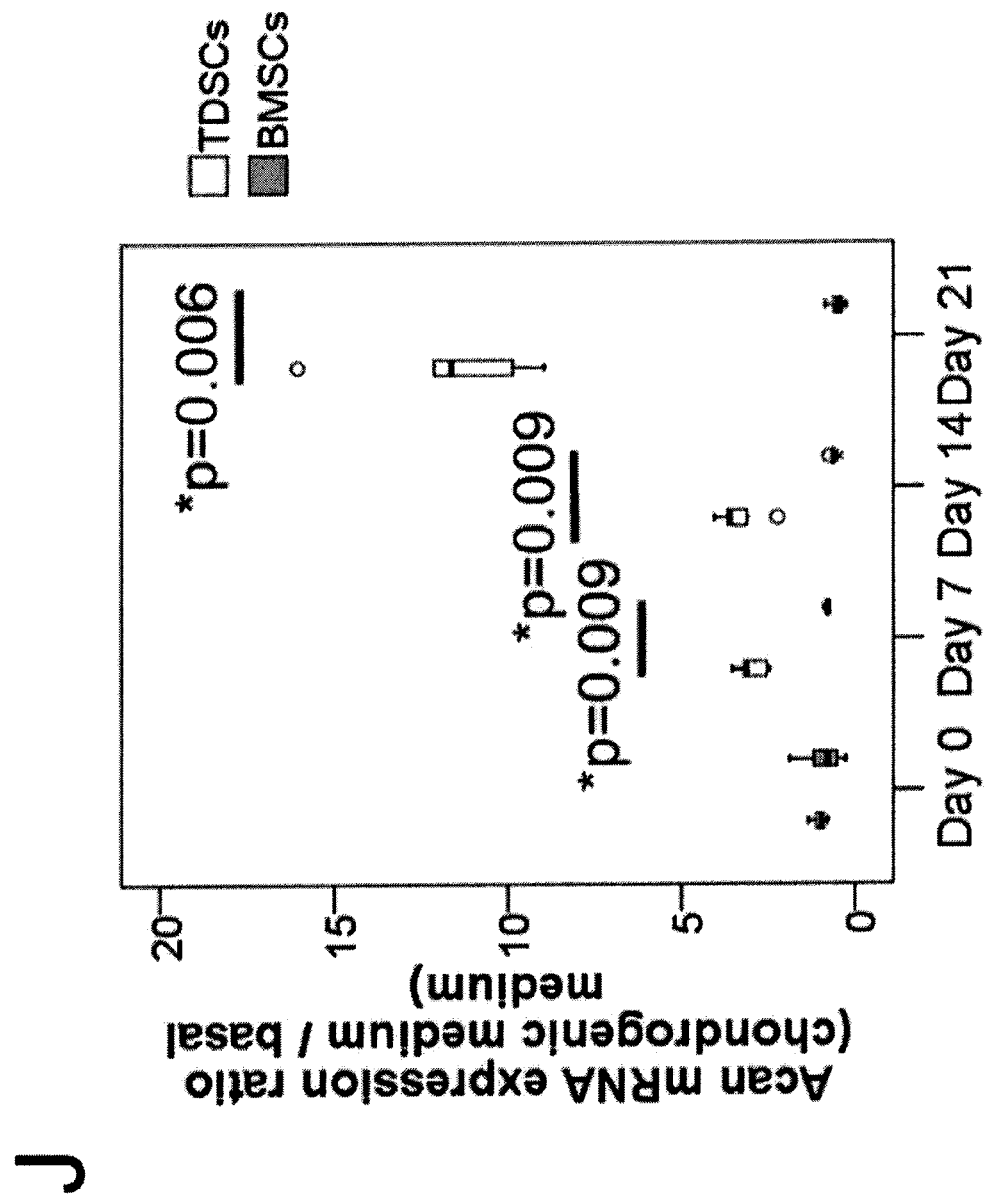
Figure 4 (continue)

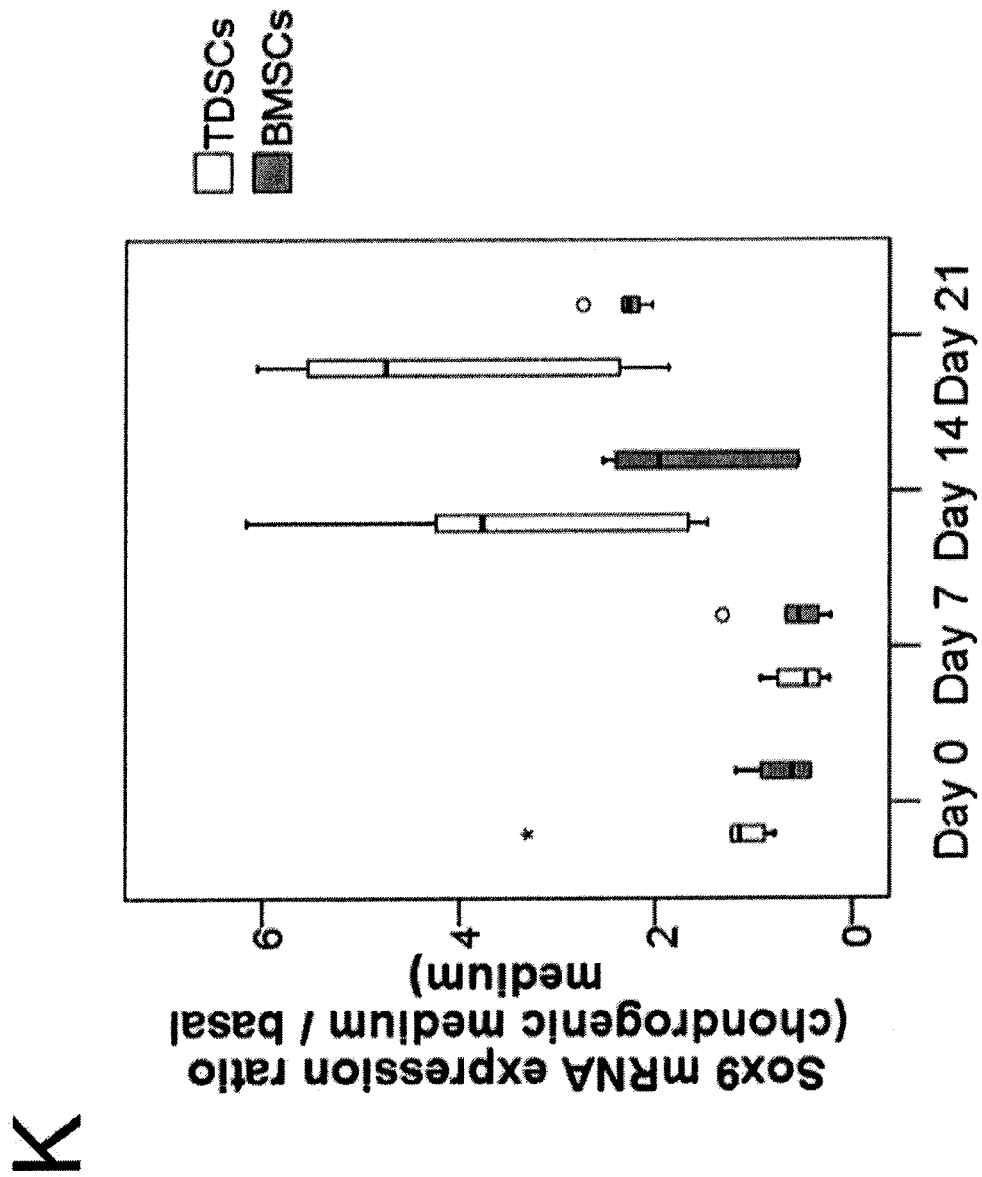
Figure 4 (continue)

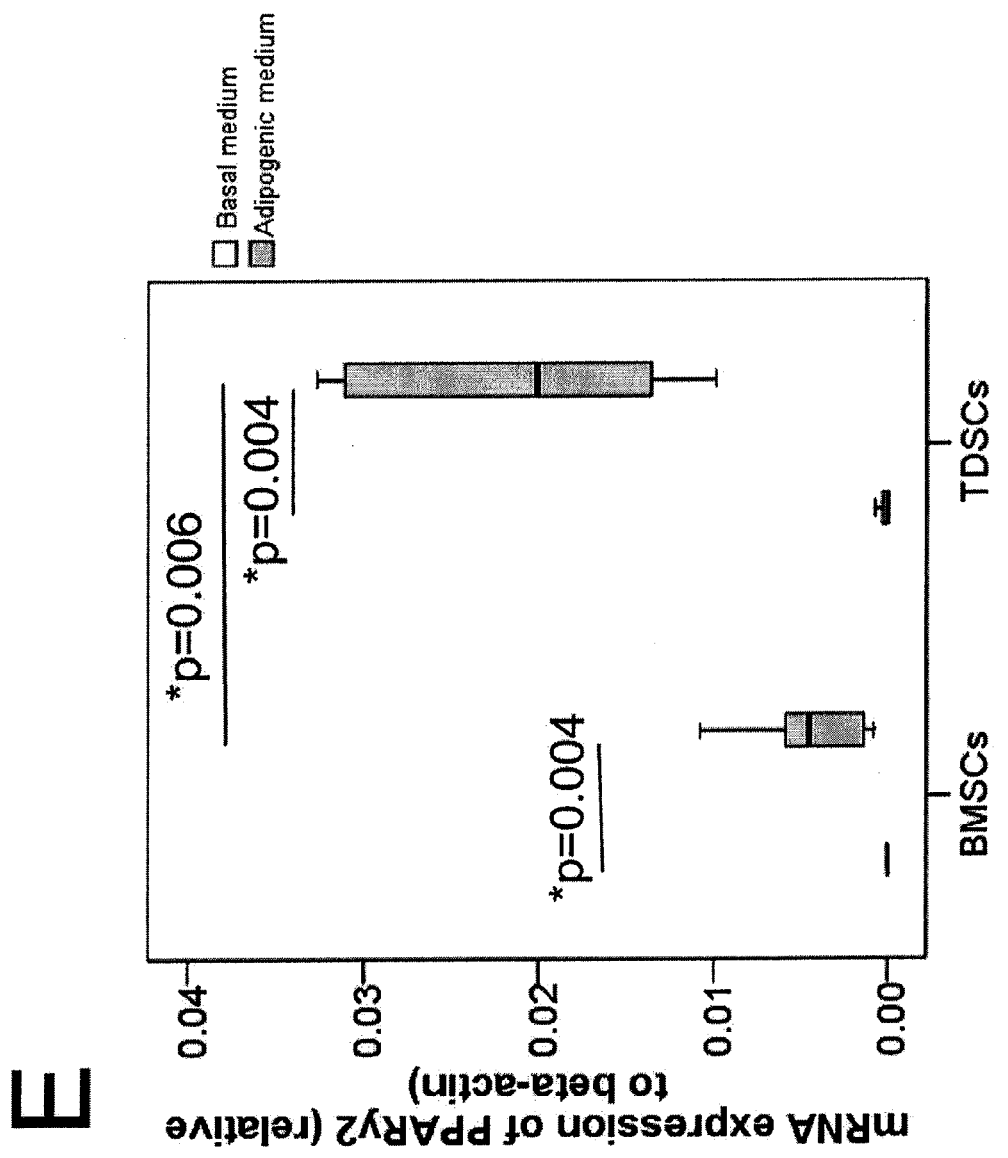
Figure 5 (continue)

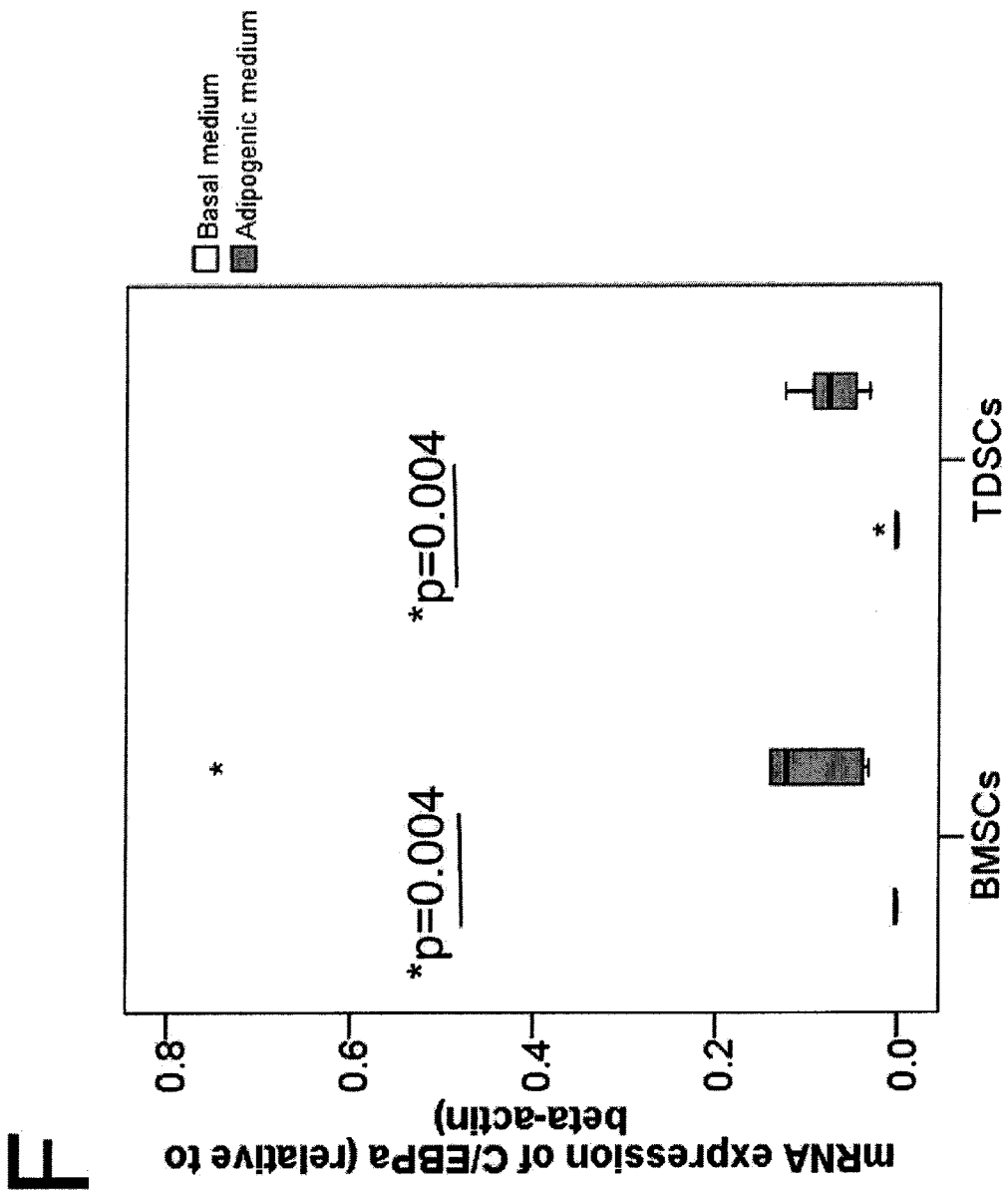
Figure 5 (continue)

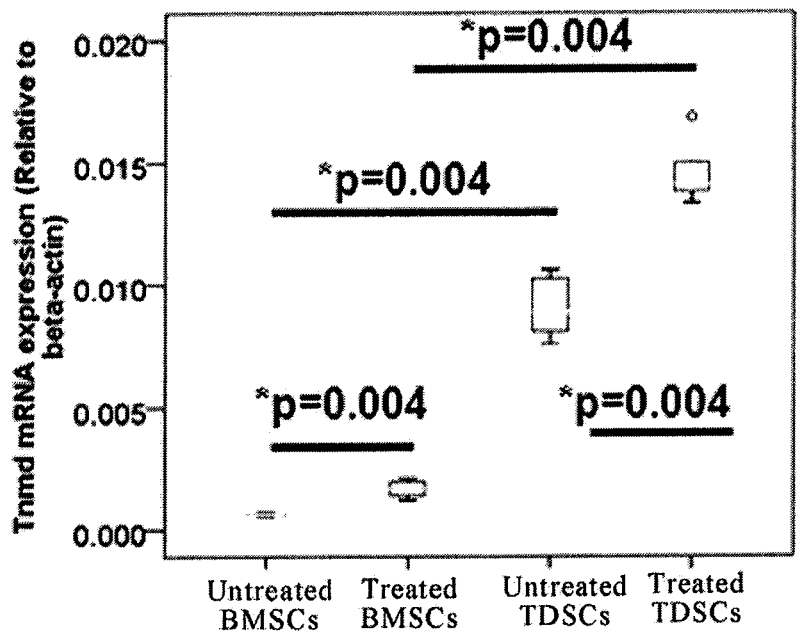
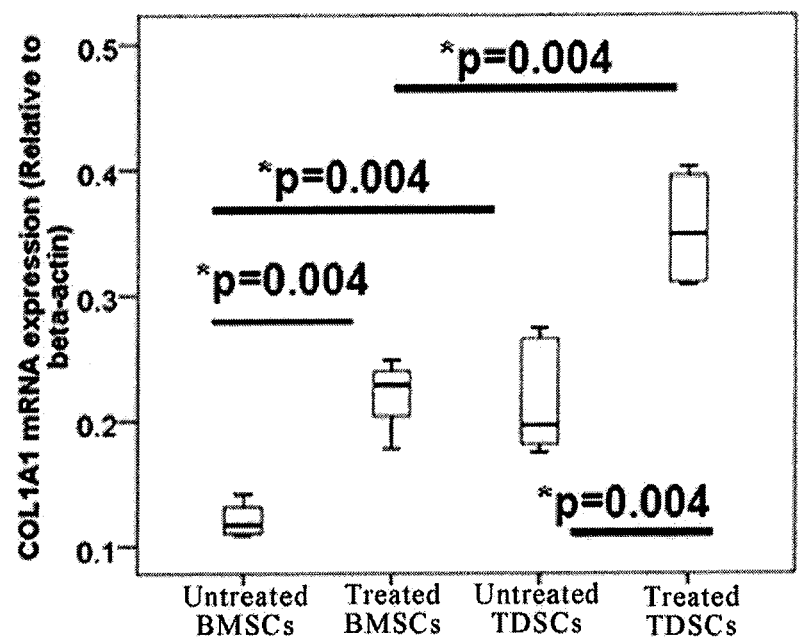
Figure 6

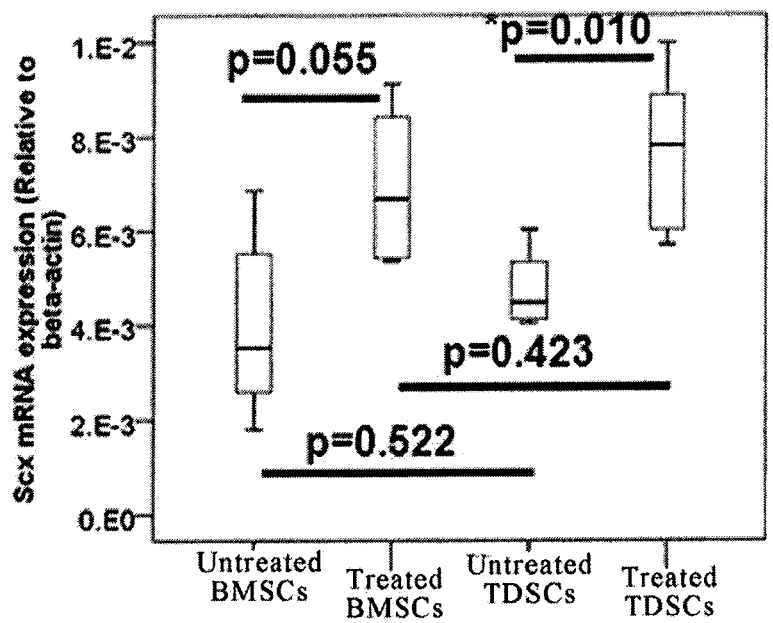
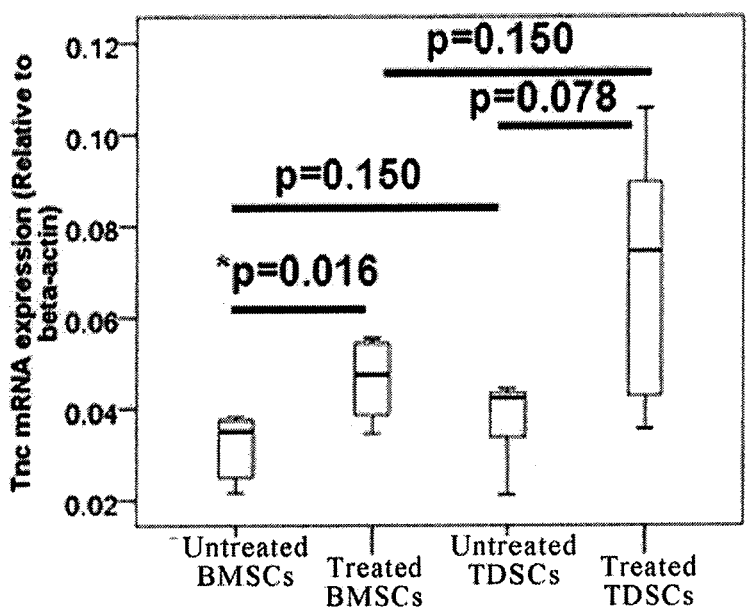
Figure 6 (continue)

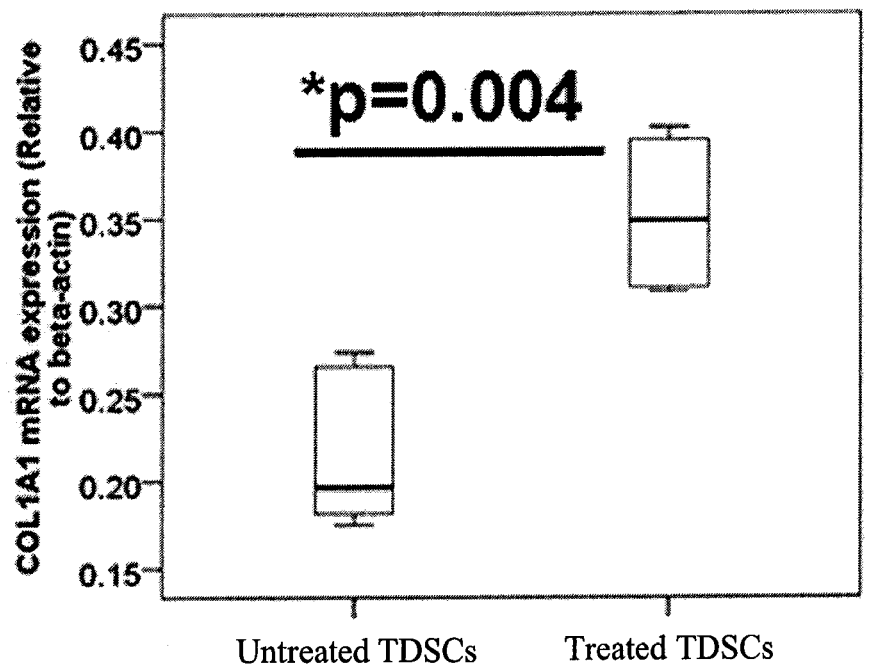
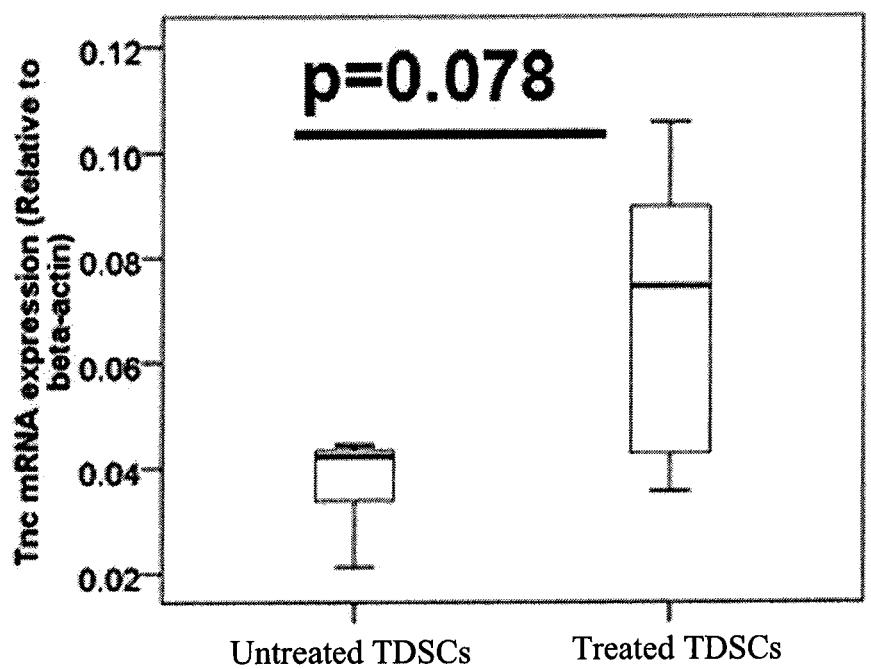
Figure 10 (continue)

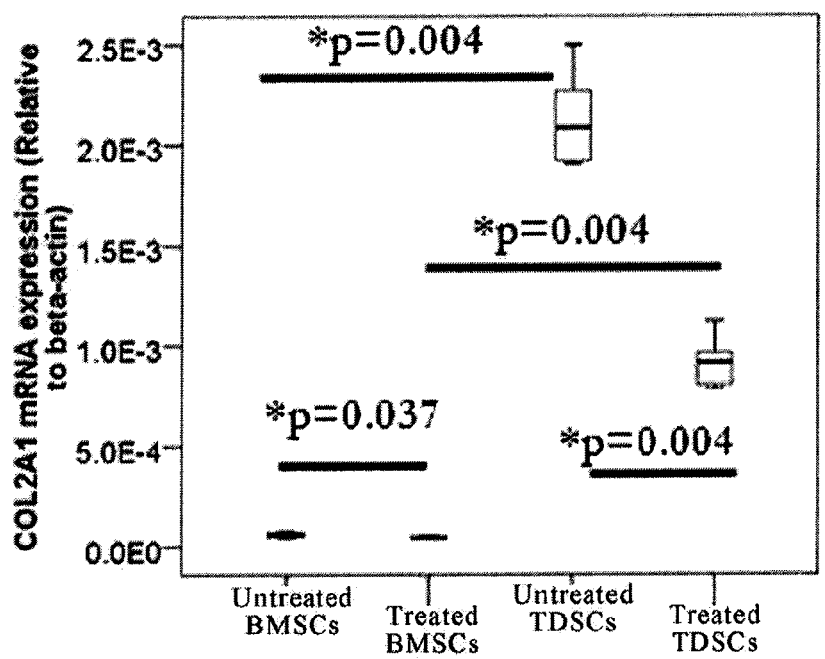
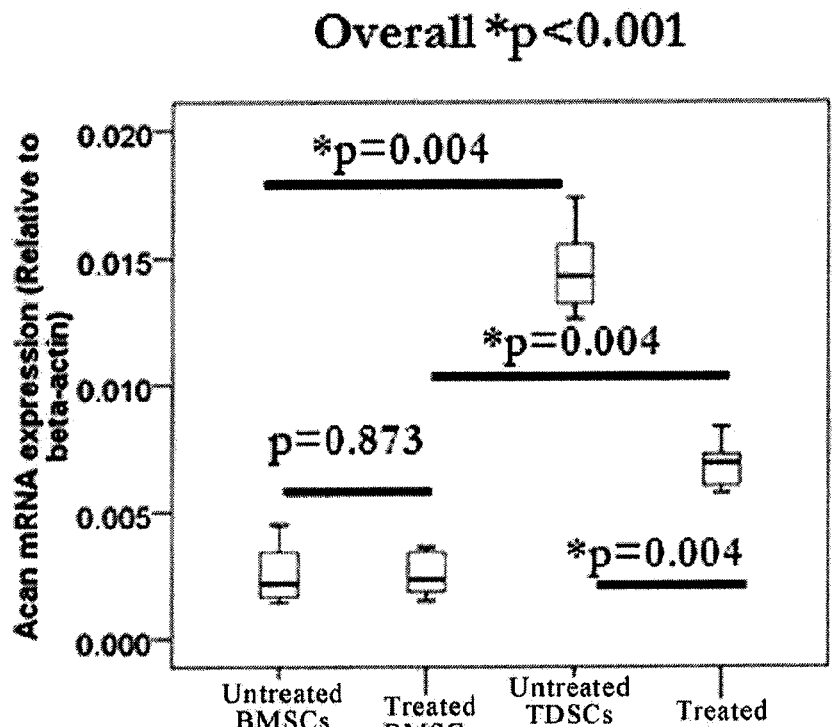
Figure 11

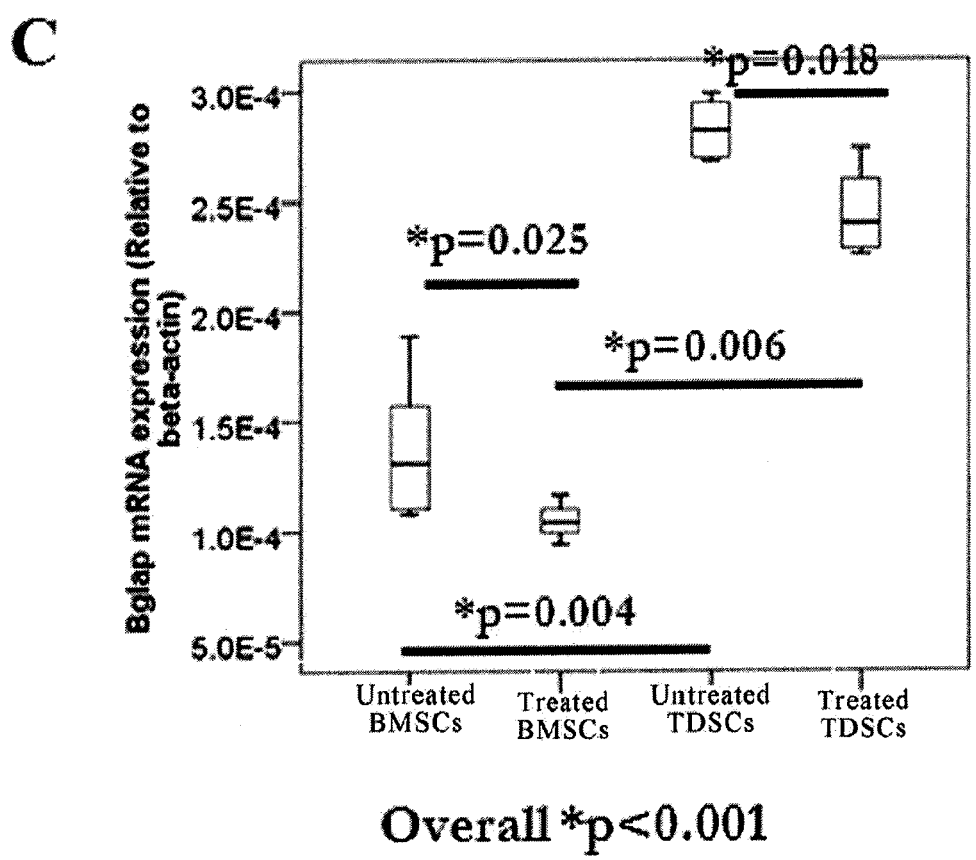
Figure 11 (continue)

Sirius Red F3BA staining
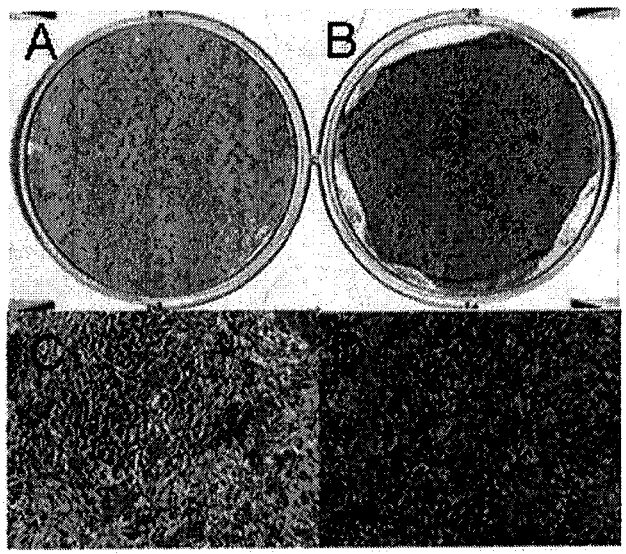
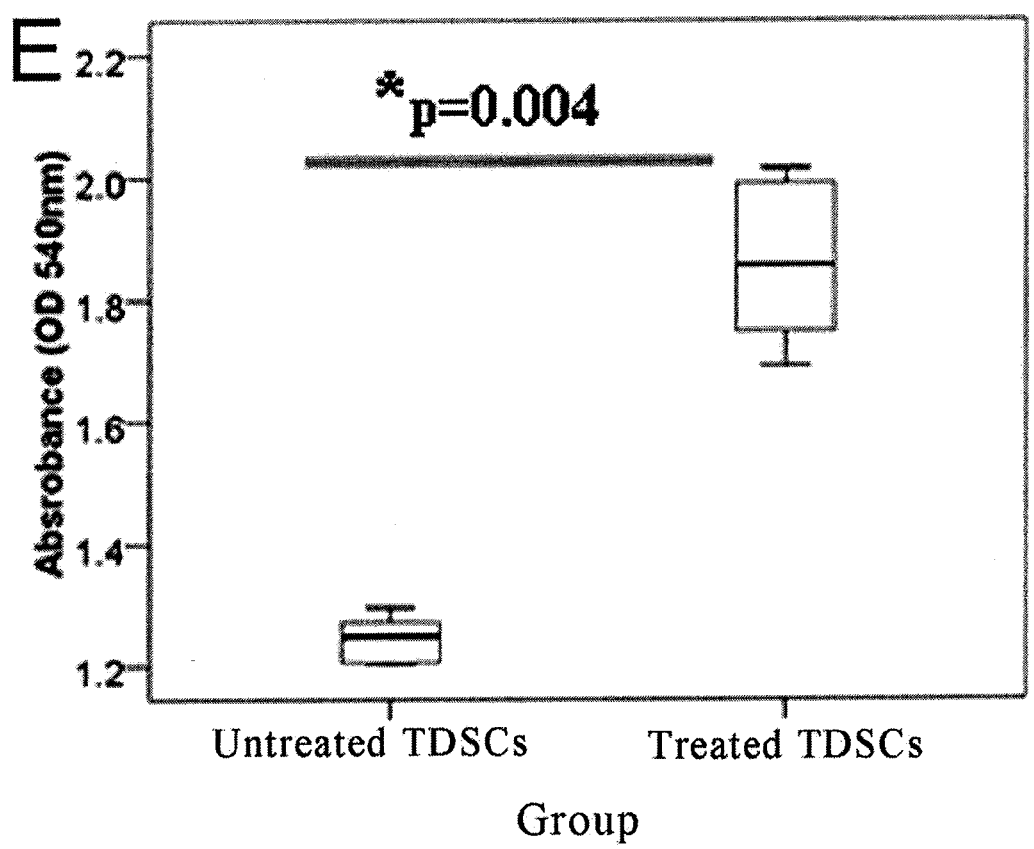
Figure 12

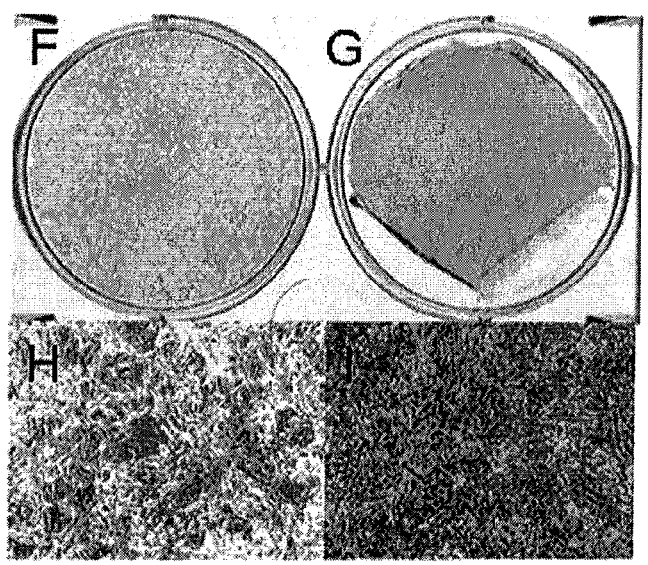
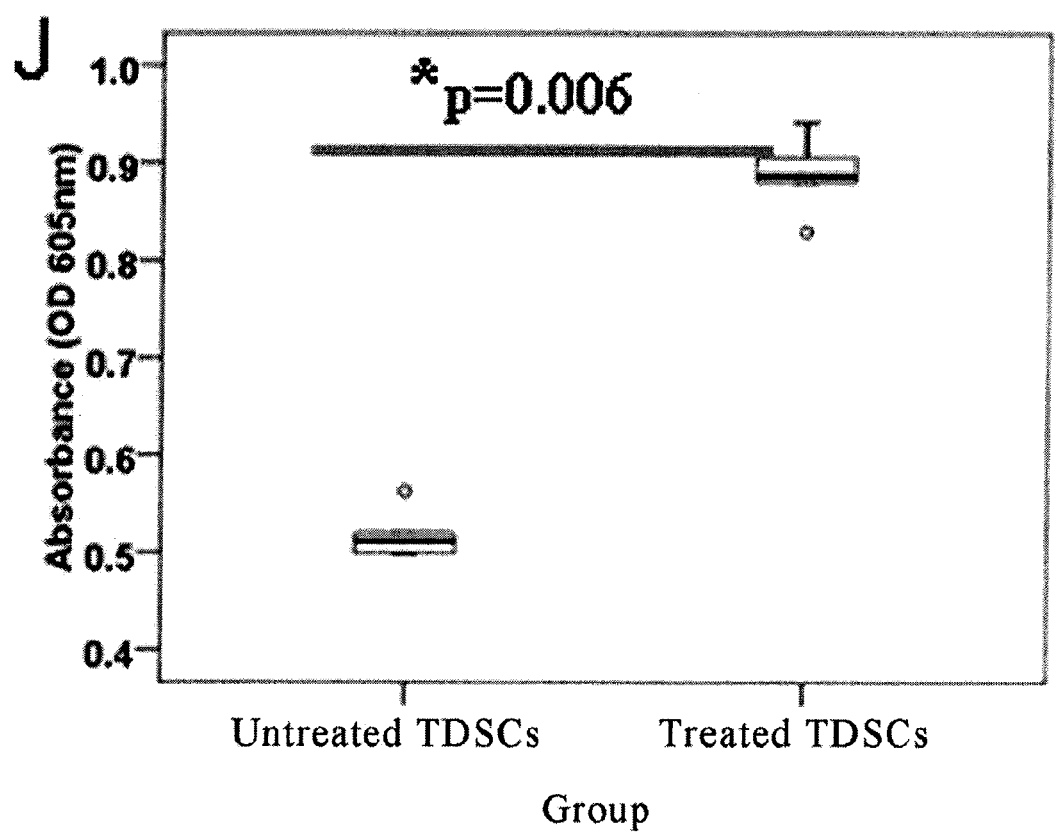
Figure 12 (continue)

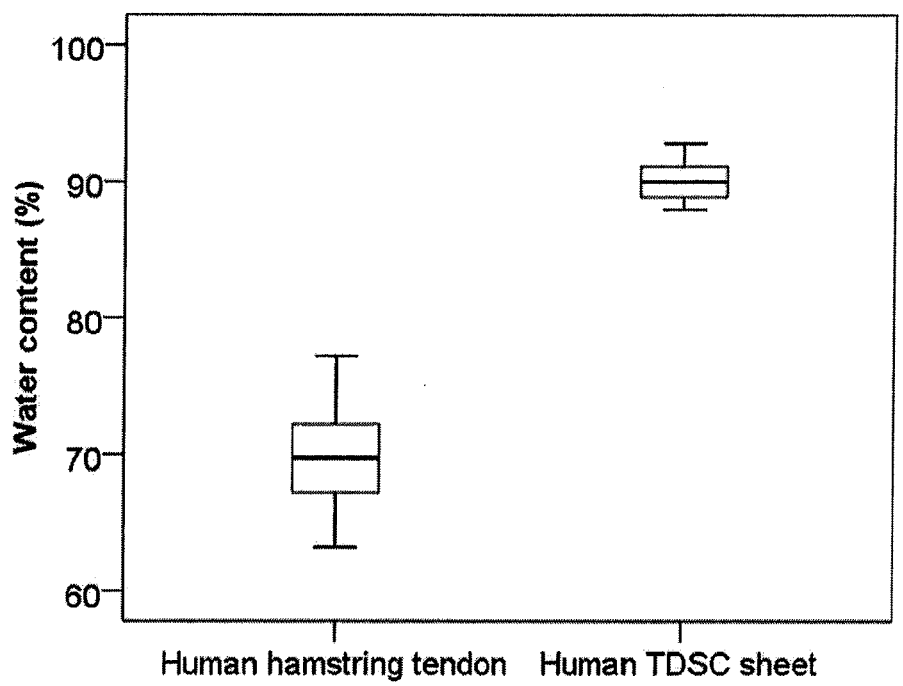
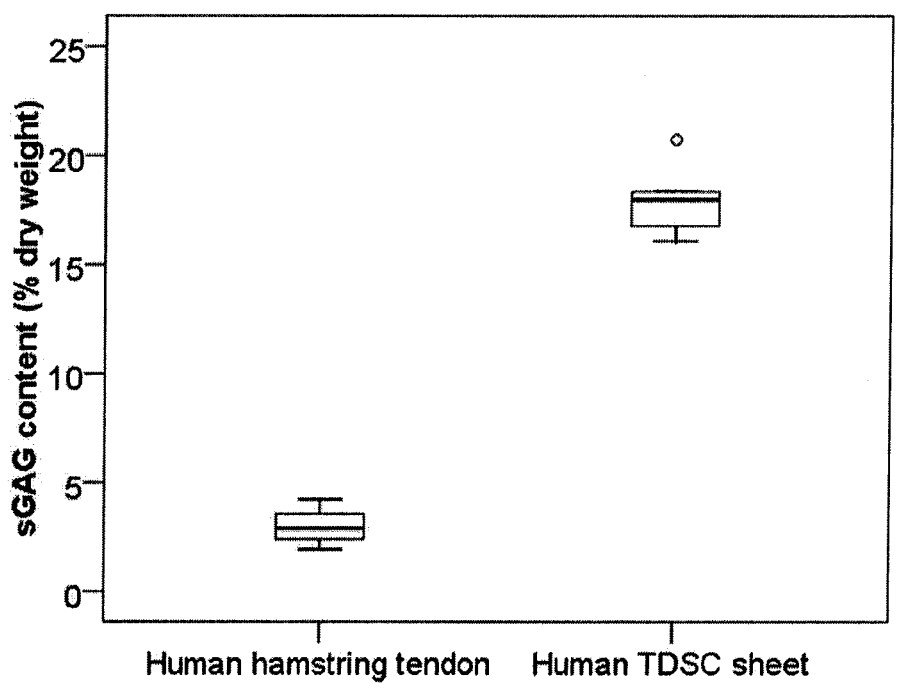
Figure 13

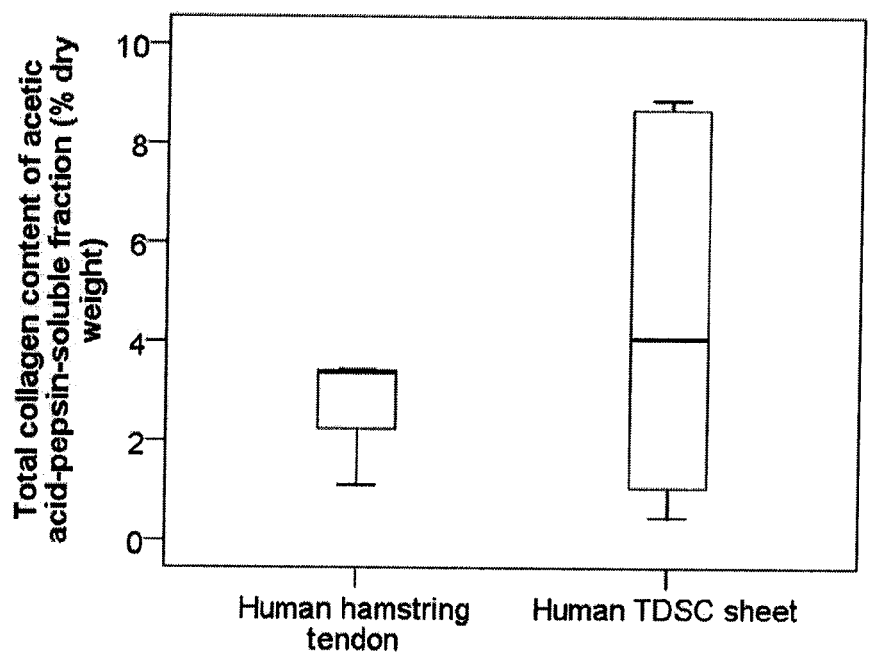
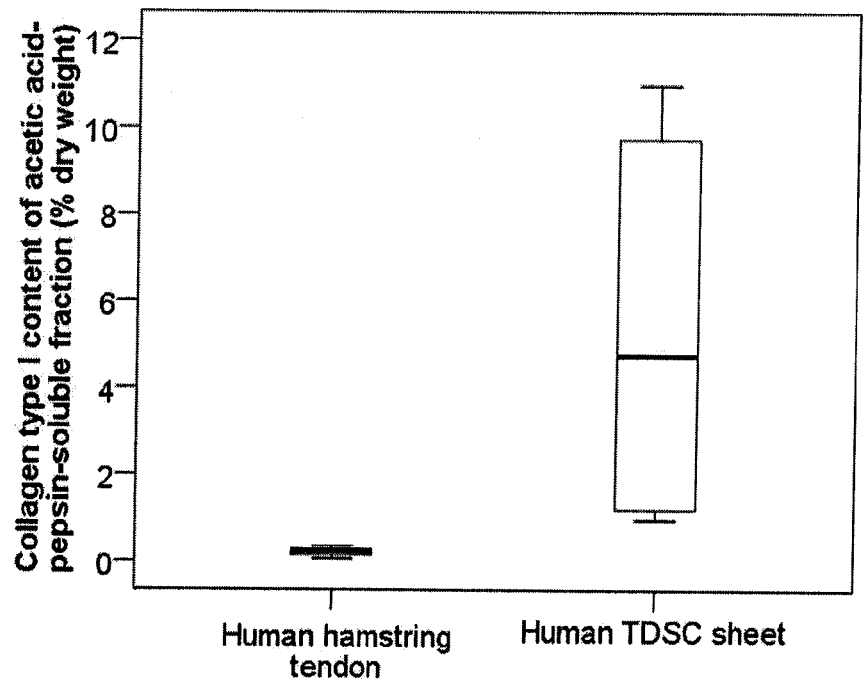
Figure 13 (continue)

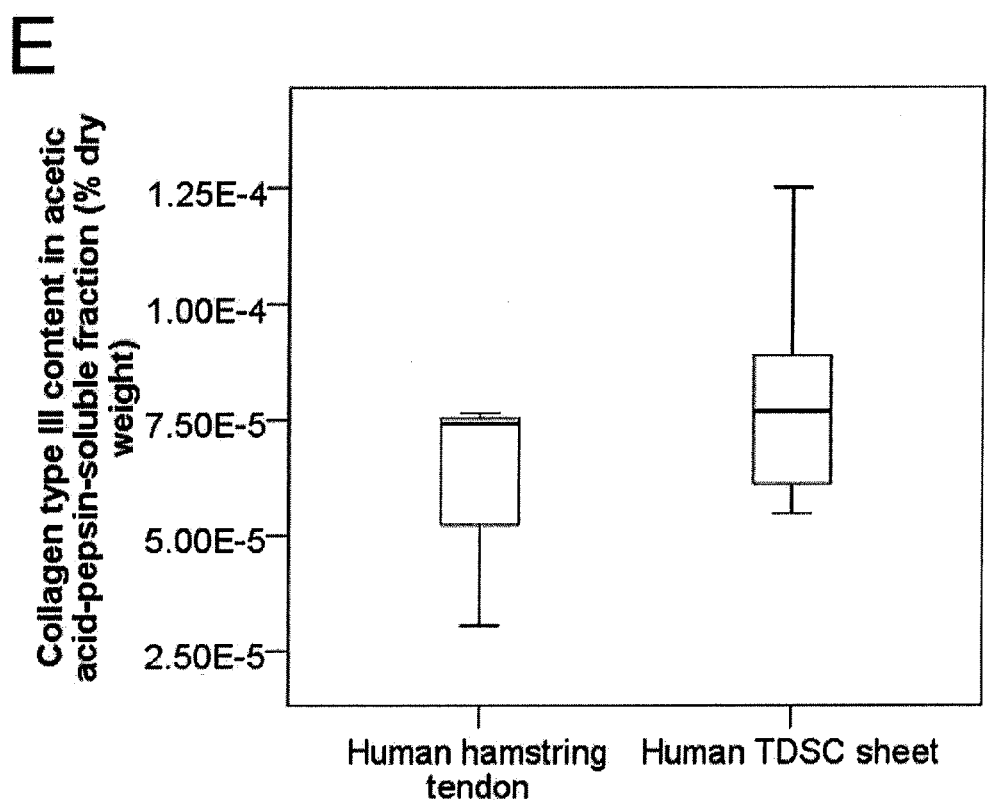
Figure 13 (continue)

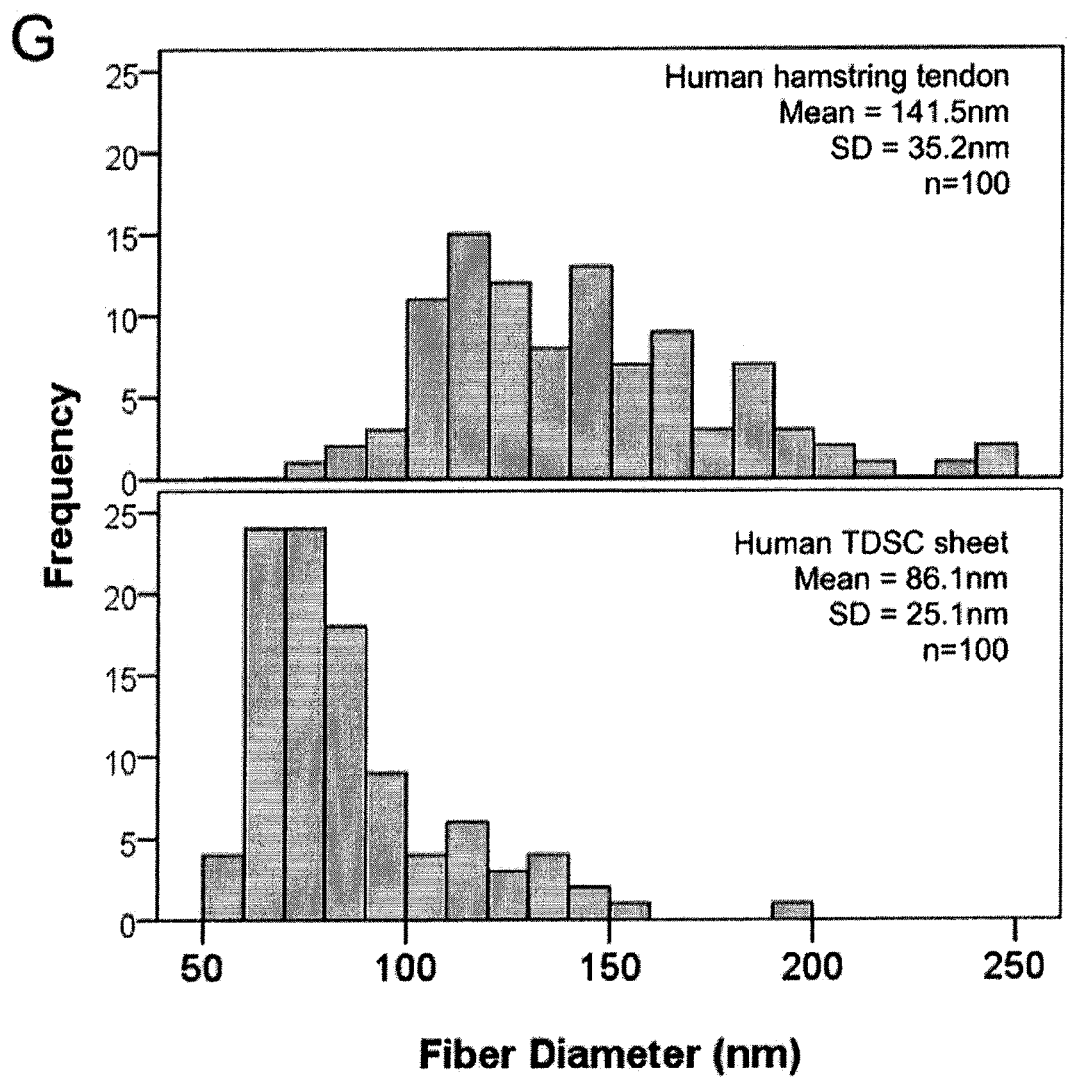
Figure 14 (continue)

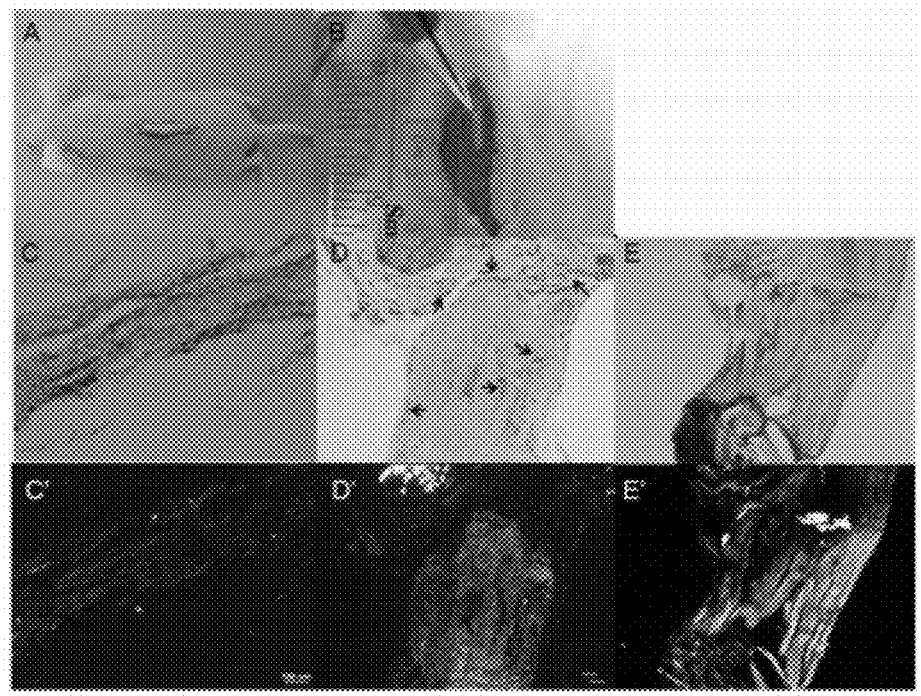
Figure 15 (A-B, C-E, C'-E')
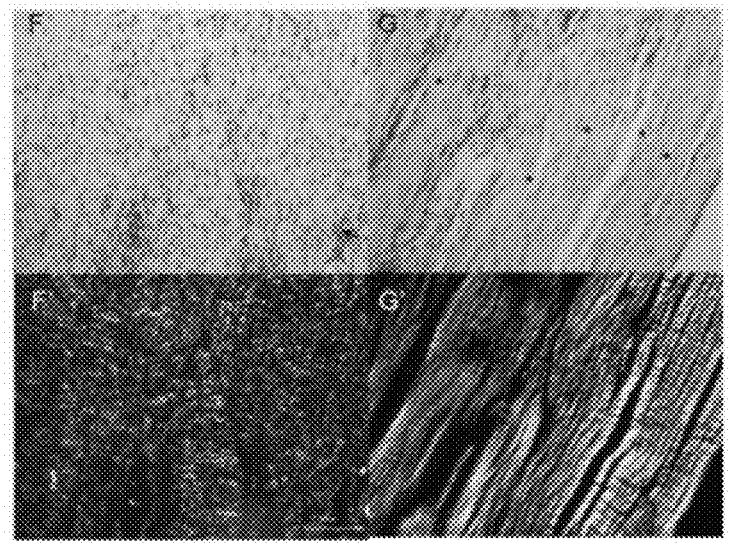
Figure 15 (F, F', G, G')

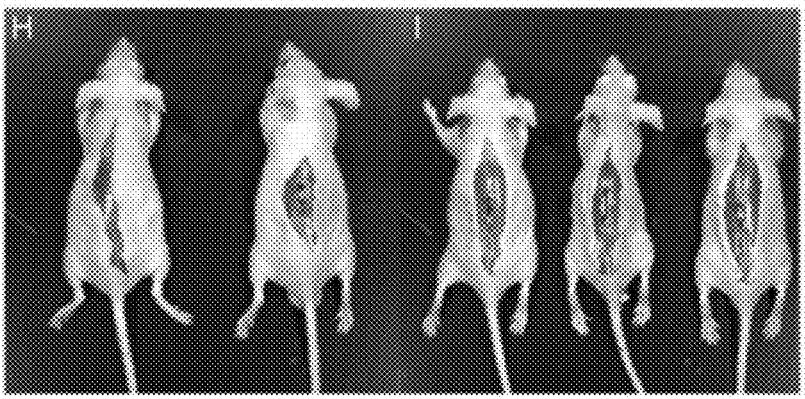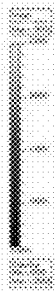
Figure 15 (H, I)
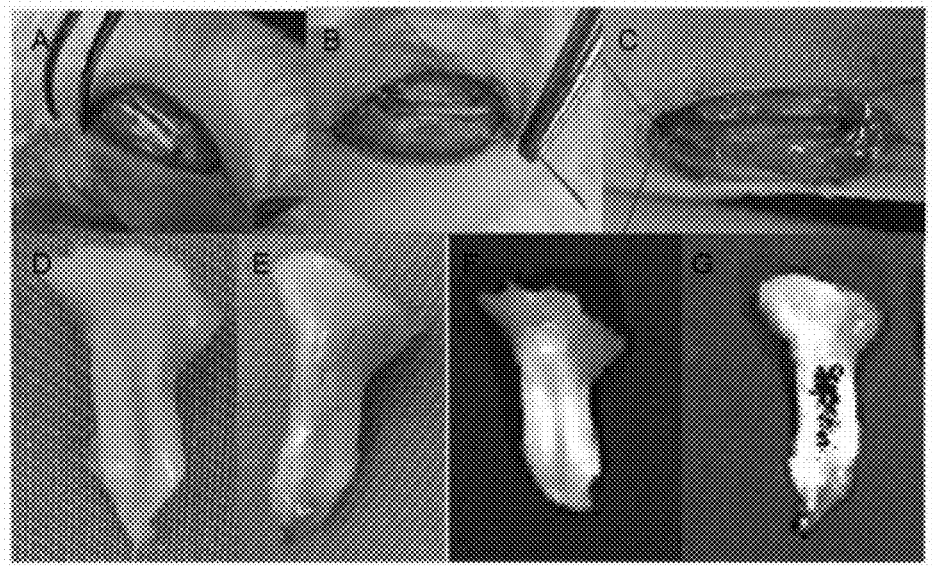
Figure 16

STEM CELL SHEET FOR TISSUE REPAIR

TECHNICAL FIELD

The present invention relates to the cell sheet and, the method of producing it and the methods of using it for the promotion of tissue repair and bio-artificial tissue engineering.

BACKGROUND

Musculoskeletal and connective tissue disorders are presenting devastating impacts on society. They are the most common causes of severe chronic, long-term pain and physical disabilities, affecting people of all ages and at a huge cost to society. One in every 3 women over age 50 will suffer from a fracture caused by osteoporosis. Every year, 23-34 million people worldwide are injured in road traffic accidents. Back pain is the $2^{nd}$ leading cause of workplace sick leave. Up to 80% of people suffer from back pain during their lives. Osteoarthritis affects over 135 million people worldwide. It is the $4^{th}$ most frequent cause of health problems in women and the $8^{th}$ in men. There are about 30 million annual tendon and ligament injuries worldwide (Maffulli et al., Clin Sports Med 2003; 22:675-692). Chronic tendinopathy accounts for 30-50% of all sports-related injuries, and almost half of all occupational illnesses worldwide.

Diseases of the skin, musculoskeletal system and connective tissue are among the leading causes of hospitalization. In USA, about $2 \times 10^5$ tendon and ligament repairs are performed annually (Pennisi. Science 2002; 295: 1011). Anterior cruciate ligament (ACL) reconstruction is the sixth most commonly performed procedure in orthopaedics (Garrett et al., J Bone Joint Surg Am 2006; 88: 660-667) and the number one surgery in sports medicine.

Tissue repair after injury is very slow and inefficient. For example, tendons do not heal by a regenerative process but via formation of a fibrotic scar after injury with diminished mechanical strength, causing significant dysfunction and disability. Surgical reattachment of tendon and bone often fails and presents difficulty for tendon to bone healing due to the lack of regeneration of the enthesis. The failure rates for rotator cuff repair have been reported to range from 20% to 94%. Similarly, ACL does not heal spontaneously after injury. ACL reconstruction, which requires a tendon graft to be put inside a bone tunnel, has failure rate ranged 10%-25%, depending on the evaluation criteria used. Osteoporotic bone has diminished capacity to heal after fractures in aged subjects. Currently, there is no cure for osteoarthritis. Hypertrophic scars of the skin formed secondary to thermal or surgical injuries cause scar contracture and functional limitation of affected tissue, restriction of growth of children and cosmetic problem.

As a result, both acute and chronic tissue injuries are difficult to manage and can result in long-term functional disability and pain, which places a chronic burden on health care systems.

Tissue injuries are commonly managed either conservatively or surgically. For example, steroid injection; physical modalities such as low-intensity pulsed ultrasound, shockwave and physiotherapy are commonly-used conservative treatments for tendon/ligament injuries. The effects of these treatments are sometimes palliative and the treatment time is usually long. If the conservative treatments fail, surgery is required for repairing the injured tissue. When the injury is severe enough, autografts, allografts, xenografts and prosthetic devices may be needed for repair or replacement of damaged tissues but have shown limited success. These methods have some inevitable disadvantages such as donor site morbidity, risk of disease transmission and tissue rejection, and limited long-term function/durability. Therefore, tissue engineering is receiving increasing attention as a potential strategy for the treatment of tissue injuries.

Tissue engineering was once categorized as a discipline under biomaterials, but has grown in scope and importance in recent years and now it is a special field in its own. It is defined as the use of a combination of cells, biomaterial and suitable biochemical and/or physio-chemical factors for repair or replacement of biological tissues. The use of tissue engineering approach for the development of functional replacement tissue for clinical use has the potential to promote tissue repair, improve the quality of healing for full restoration of tissue function and reduce the chance of tissue re-injuries.

Cells and scaffold are the two most essential components of tissue engineering. Among different possible cell sources for tissue engineering, mesenchymal stem cells (MSCs)-derived from the bone marrow (BMSCs) were commonly used (Chong et al., J Bone Joint Surg Am 2007; 89: 74-81; Hankemeier et al., Arch Orthop Trauma Surg 2007; 127(9): 815-821) because these cells maintain some degree of self-renewal potential and have the capacity to differentiate into cells of multiple mesenchymal lineages. The synthetic and proliferative abilities of these cells are also robust (Liu et al., Biomaterials 2008; 29: 1443-1453; Ge et al., Cell Transplant 2005; 14: 573-583). Despite these encouraging findings, there is a chance that the MSCs might not differentiate towards the target tissue type or induce tumor formation. For instance, transplantation of BMSCs into the rabbit tendon defect was reported to form ectopic bone and expressed alkaline phosphatase activity in constructs (Awad et al., J Orthop Res 2003; 21: 420-431; Harris et al., J Orthop Res 2004; 22: 998-1003). Tumor induction by undifferentiated BMSCs was reported in some specific circumstances (Tasso et al., Carcinogenesis 2009; 30(1): 150-157). The in vitro differentiation of stem cells towards tissue-specific lineage before transplantation might be a good strategy to promote tissue healing while minimizing the chance of erroneous cell differentiation and tumor induction. However, a method of controlling the differentiation of MSCs to target progenitor cells remains a great challenge which hinders their application.

Although stem cells isolated from different tissues share many important stem cell characteristics, certain properties of stem cells are affected by their origins (Sakaguchi et al., Arthritis Rheum 2005; 52: 2521-2529). The selection of appropriate stem cell source is important for successful tissue engineering. Recently, stem cells have been isolated in tendon (Bi et al., Nat Med 2007; 13(10) 1219-1227). The inventors were the first group to report the isolation and characterization of tendon-derived stem cells (TDSCs) from rat (Rui et al., Tissue Eng Part A 2010; 16(5): 1549-1558). The tendon stem cells present new opportunity for repairing damaged tissues and bio-artificial tissue engineering.

As mentioned, in vitro differentiation of MSCs into tissue-specific progenitors prior to transplantation is a possible approach to circumvent the problems of erroneous cell differentiation and tumor formation while promoting tissue regeneration. Different factors have been reported to have effects on cell differentiation including growth factors, mechanical stimulation, composition and topographical cues from biomaterials, co-culture with tissue-specific cell types and gene modification. Hence they might be suitable for in vitro differentiation of MSCs into tissue-specific progenitors.

The composition and properties of biomaterials used as scaffold for tissue engineering can significantly affect the regeneration of neo-tissues. There are different categories of scaffolding materials for tissue engineering: polyesters, polysaccharides and collagen derivatives and calcium phosphate derivatives.

Synthetic scaffolds such as polyglycolic acid (PGA), polylactic acid (PLA) and their copolymer polylactic-co-glycolic acid (PLGA) have been used for bone and tendon tissue engineering. They are attractive because their degradation products, glycolic acid and lactic acid, are natural metabolites and they have good mechanical properties as well as outstanding processability. As they are manufactured from chemical compounds, they permit better control of chemical and physical properties and hence quality. However, biocompatibility of these synthetic scaffolds is very poor as they do not support a high level of cell adhesion (Zhu et al., J Biomed Mater Res 2002; 62: 532-539) and the natural metabolites are acidic in high concentrations which may result in local inflammatory reaction.

On the other hand, biological scaffolds such as relatively pure natural collagen derivatives and the complex decellularized extracellular matrix materials with multiple natural macro-molecules such as small intestinal submucosa (SIS) (Dejardin et al., Am J Sports Med 2001; 29: 175-184) and silk (Altman et al., Biomaterials 2002; 23(20): 4131-4141), are highly biocompatible and also exhibit superior bio-functionality. Limitations of these biological scaffolds are low mechanical properties (Gentleman et al., Bioamterials 2003; 24: 3805-3813). Their processabilities are also limited (Gentleman et al., Bioamterials 2003; 24: 3805-3813). High batch-to-batch variation also makes a reliable production of these scaffolds difficult (Koski et al., Orthop Clin Nort Am 2000; 31: 437-452). They may cause inflammatory response, implant rejection (Koski et al., Orthop Clin Nort Am 2000; 31: 437-452) and have risk of disease transmission (Chen et al., Stem Cells 2009; 27(6): 1276-1287).

Calcium phosphate derivatives such as the hydroxapetite and tri-calcium phosphate (TCP) are commonly used as scaffolding materials for bone regeneration. These materials usually take long time for degradation.

Accordingly, a need exists for finding the appropriate cell types and scaffold materials for the promotion of tissue repair or engineering of bio-artificial tissue for replacement of damaged tissue.

SUMMARY

One aspect disclosed herein is related to a cell sheet derived from a stem cell for the promotion of tissue repair and bio-artificial tissue engineering.

In an embodiment, the cell sheet, disclosed herein comprises treated stem cells and self-secreted extracellular matrix thereof in which the treated stem cells are embedded.

In another embodiment, the cell sheet as disclosed herein comprises about 50-95% w/w water, and therefore the dry weight of the cell sheet is about 5-50% w/w based on the total weight of the sheet. The cell sheet can comprise compounds selected from the group consisting of collagen; proteoglycan; glycoprotein; or any combination thereof. In a preferred embodiment, the collagen is selected from the group consisting of Collagen type I, Collagen type II, Collagen type III or any combination thereof. In another preferred embodiment, the proteoglycan is selected from the group consisting of aggrecan, decorin, biglycan or any combination thereof. In still another preferred embodiment, the glycoprotein is selected from the group consisting of elastin, cartilage oligomeric matrix protein (COMP), tenascin C or any combination thereof.

In still another embodiment, the cell sheet is free of cells, i.e. an acellular product of the cell sheet. The composition or the structure of the cell sheet free of cell or the acellular sheet is the same as the cell sheet as disclosed herein but is free of cell. The acellular sheet can be used alone or in combination with other cell types or growth factors for the promotion of tissue repair or tissue engineering application.

In another embodiment, the stem cell as used in the invention is an adult stem cell. The stem cell, such as an adult stem cell, can be isolated from animal or human tissues. The stem cell used for the production of the cell sheet is autologous or allogeneous. In the embodiments of the invention, the stem cell is isolated from, but not limited to, tendon/ligament tissue, bone morrow, adipose tissue or dental pulp. In one embodiment of the invention, the cell sheet is chemically, biologically, genetically, biomechanically and/or biophysically modified and/or added with biomaterials such that the modification modulates the degree and activity of the cell or the cell sheet. Stem cell, such as tendon-derived stem cell (TDSC), proliferates fast and shows high colony-forming ability and exhibits high osteogenic, chondrogenic, adipogenic and tenogenic differentiation potential and produces high level of ECM, has the advantage of shortening the in vitro cell culture time for clinical application.

In other embodiments, the cell sheet as disclosed herein is formed by a method comprising the steps of isolating stem cells, expanding the stem cells and treating the stem cells with biological factors or factors leading to a production of biological factors by the treated stem cells and/or a maturation of the cell sheet, whereby inducing a differentiation of the stem cells, a production of their own extracellular matrix and forming a cell sheet in vitro.

In one embodiment, the biological factors are proteins made of amino acids that modulate the biological activities of the stem cells. One example of the biological factors to induce the formation of the cell sheet belong the Transforming Growth Factor family (TGF) such as TGF-β, together with ascorbic acid. Another example of the biological factors belongs to the Growth Differentiation Factor/Bone Morphogenetic Protein (GDF/BMP) family members such a GDF-5/BMP-14, GDF-6/BMP-13 and GDF-7/BMP-12, together with ascorbic acid. Yet another example of the biological factors is Connective Tissue Growth Factor (CTGF) and ascorbic acid.

In still another embodiment, a chemical agent can be additionally used to induce the stem cell to produce the biological factors and the other biological factors. In still another embodiment, by genetic modification, the stem cell is able to over-express the biological factors as disclosed herein or the other biological factors. In an alternative embodiment, the induction of biological factors or other biological factors is simulated by using biophysical modalities. In another alternative embodiment for formation of cartilage, compression is used as a mechanical force in addition to the biological and chemical factors to simulate the formation of cartilage. In still another alternative embodiment for bone healing, tensile load is applied to the cell to assist the healing of bone or tendon or ligament.

Another aspect disclosed herein is use of the cell sheet as disclosed herein as a bioactive material for the promotion of tissue repair. The cell sheet, optionally together with biomaterials, chemical factors, biological factors, genetic factors, biomechanical factors, biophysical factors in vitro and/or in vivo maturation in an animal, preferably an immunodeficiency animal, such as a nude mouse, or in an animal to which the cell sheet is autologous, forms a bio-artificial material for tissue repair. In one embodiment, the cell sheet of the invention, with an active stem cell, is used for enhancing the repair of window injury in the patellar tendon after removal of the patellar bone-patellar tendon-bone graft in anterior cruciate ligament (ACL) reconstruction by rolling and suturing the cell sheet in the window defect. In another embodiment, the cell sheet is used to enhance suture repair of tendon (e.g. Achilles tendon, hand tendon) and ligament (e.g. posterior cruciate ligament, PCL; ACL) by wrapping the cell sheet around the rupture site. It is applied to promote tendon-bone junction regeneration in ACL reconstruction by wrapping the tendon graft with the cell sheet, similar to the use of periosteal autograft by other groups (Ohtera et al., Crit Rev Biomed Eng 2000; 28(1-2): 115-118; Youn et al., Clin Orthop Relat Res 2004; 419: 223-231; Chen et al., J Orthop Surg Taiwan 2003; 20: 21-29). In still another embodiment, the cell sheet is used for rotator cuff repair by suturing the cell sheet to the interface between tendon and bone. In yet another embodiment, the cell sheet is used for the repair of bone condition or disease such as bone fracture, cartilage condition or disease such as osteoarthritis or osteo-chondro defect, muscle condition or disease such as muscle tear, skin condition or disease such as wound or burn, by putting the cell sheet in the defect.

Still another aspect disclosed herein is use of the acellular product of the cell sheet alone or in combination with other cell types or growth factors for the promotion of tissue repair. The cell sheet is used as an acellular biomaterial for tissue engineering application similar to the above after decellularization. It is used to prevent repair gap formation or failure, enhance host cell attachment, infiltration and proliferation. The cell sheet as disclosed herein can be used as a decellularized product together with other known growth factors and cell types for the promotion of tissue repair.

Still another aspect disclosed herein is use of the cell sheet as disclosed herein to form a bio-artificial organ for tissue replacement. The cell sheet, together with biomaterials, chemical factors, biological factors, genetic factors, biomechanical factors, biophysical factors in vitro and/or in vivo maturation in an animal, preferably an immunodeficiency animal, such as a nude mouse, or in an animal to which the cell sheet is autologous, forms a bio-artificial organ for tissue replacement. In one embodiment, after rolling the cell sheet and loading it on a U-shape spring in vitro, followed by further growth in a nude mouse model, a tendon-/ligament-like tissue is formed. Further modifications of the in vitro culture procedures such as application of in vitro mechanical load, or combination with other biomaterials or growth factors can further improve the tissue structure for bio-artificial organ engineering.

Other objects and advantages of the present inventions will become apparent from the following detailed description when read in conjunction with the accompanying figures.

BRIEF DESCRIPTION OF THE FIGURES

The patent or application file contains at least one drawing executed in color. Copies of this patent or patent application publication with color drawing(s) will be provided by the Office upon request and payment of the necessary fee.

Drawing described below are intended for purposes of illustration only and are not intended to limit the scope of the inventions.

FIG. 1(C) illustrates the proliferative potential of paired rat TDSCs and rat BMSCs at day 2 with BrdU assay (n=12). *p≤0.050

Figure 1:
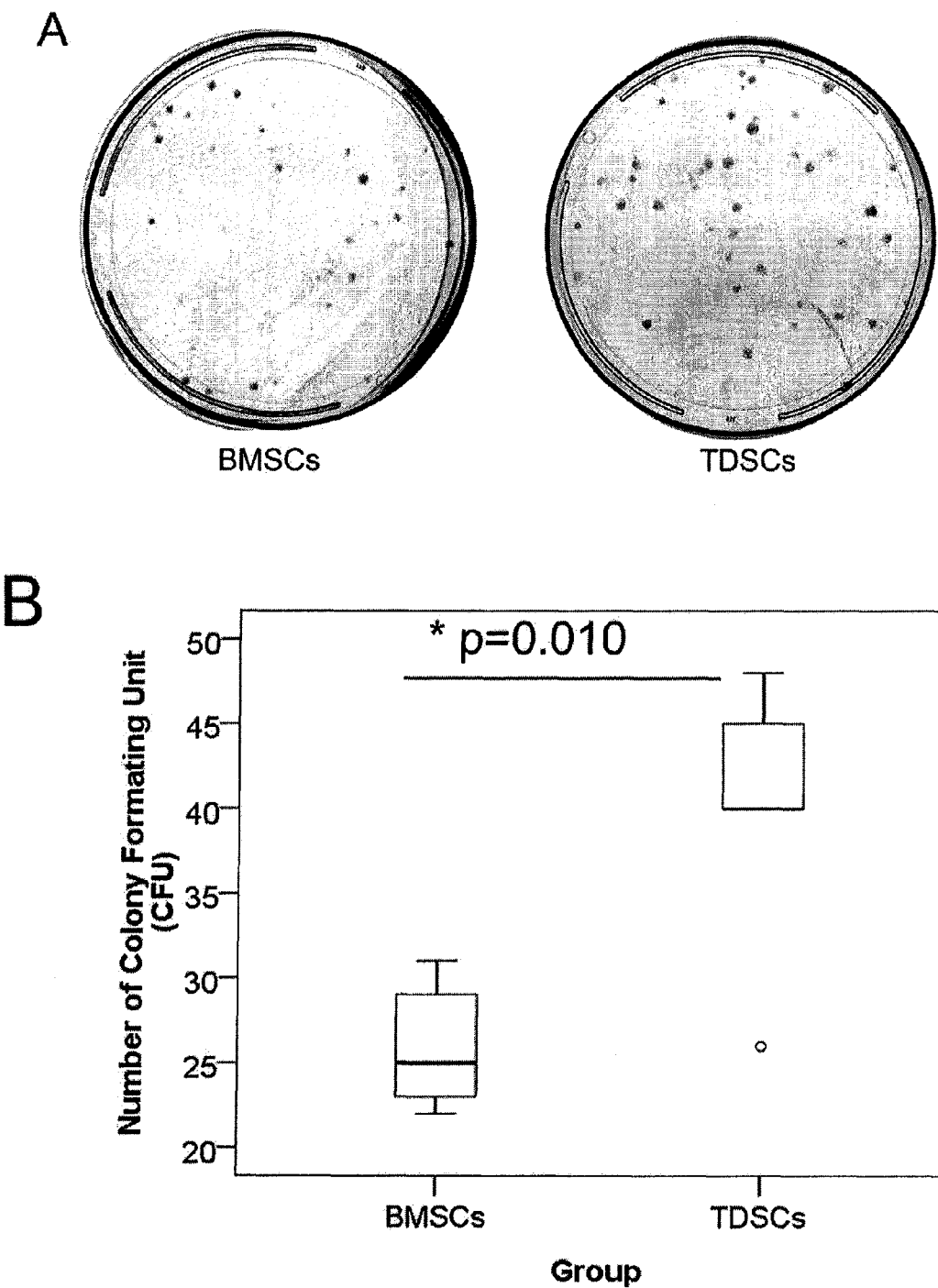
FIGS. 1(A & B) illustrates the comparison of colony-forming ability of paired rat TDSCs (TDSCs) and rat BMSCs (BMSCs) isolated from green fluorescence protein (GFP) rats at day 10 (100 cells in 10 cm$^2$ dish) (n=5).

Rat TDSCs formed more colonies (p=0.010) (FIG. 1A, B) and proliferated faster (p<0.001) (FIG. 1C), compared to rat BMSCs.

Figure 2:
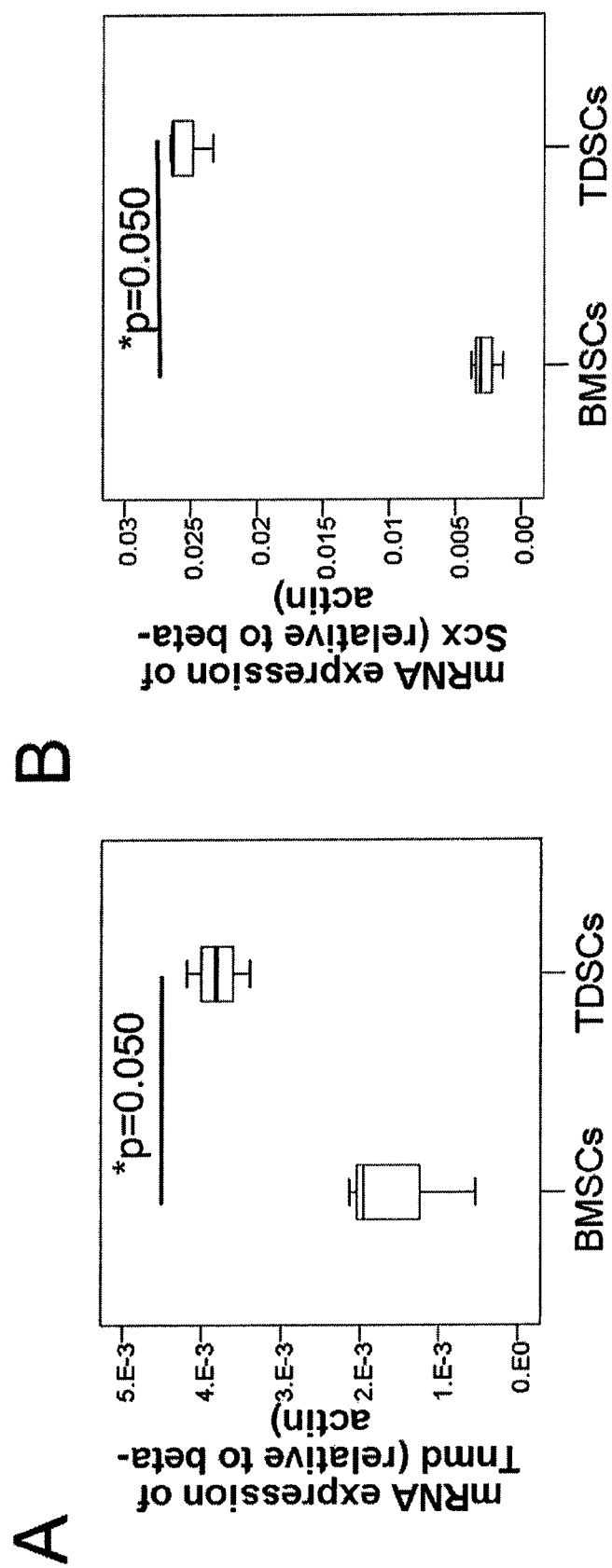

FIG. 2(A-H) illustrates the mRNA expression of (A) tenomodulin (Tnmd); (B) scleraxis (Scx); (C) collagen type I alpha 1 (Col1A1); (D) collagen type III alpha 1 (Col3A1) (E) ratio of Col1A1Col3A1; (F) decorin (Dcn); (G) tenascin C (Tnc); (H) alkaline phosphatase (Alpl); (I) collagen type II alpha 1 (Col2A1), (J) aggrecan (Acan) and (K) biglycan (Bgn) in paired rat TDSCs and rat BMSCs isolated from GFP rats in basal complete medium. *p≤0.050

Rat TDSCs expressed higher mRNA level of tenogenic (Tnmd, Sex, Col1A1, Dcn, Bgn), chondrogenic (Col2A1) and osteogenic (ALP) markers, compared to paired rat BMSCs in basal complete medium (all p=0.050). There was a trend of lower mRNA expression of Col3A1 and higher expression of Tnc and Acan in TDSCs compared to BMSCs but the difference was not statistically significant.

FIG. 3(A-D) illustrates the Alizarin red S staining of calcium nodules in (A, C) rat BMSCs and (B, D) rat TDSCs isolated from GFP rats in (A, B) basal or (C, D) osteogenic induction media after 21 days. Magnification: 100×. Scale bar=100 μm FIG. 3(E) illustrates the quantitative analysis of the Alizarin red S stain bound to calcium nodules. FIG. 3(F-J) illustrates the mRNA expression of (F) Alpl, (G) Runx2, (H) Bmp2, (I) Spp1 and (J) Bglap in paired rat TDSCs and rat BMSCs in basal medium or osteogenic medium for 21 days. *p<0.050

More calcium nodules were formed in rat TDSCs compared to rat BMSCs upon osteogenic induction. There was significantly higher expression of Alpl, Runx2, Bmp2 and Bglap in rat TDSCs compared to that in rat BMSCs at day 21 in basal medium (all p=0.004). There was significantly higher expression of Alpl (p=0.006), Runx2 (p=0.006), Bmp2 (p=0.011), Spp1 (p=0.006) and Bglap (p=0.006) in rat TDSCs compared to that in rat BMSCs at day 21 upon osteogenic induction.

Figure 4:
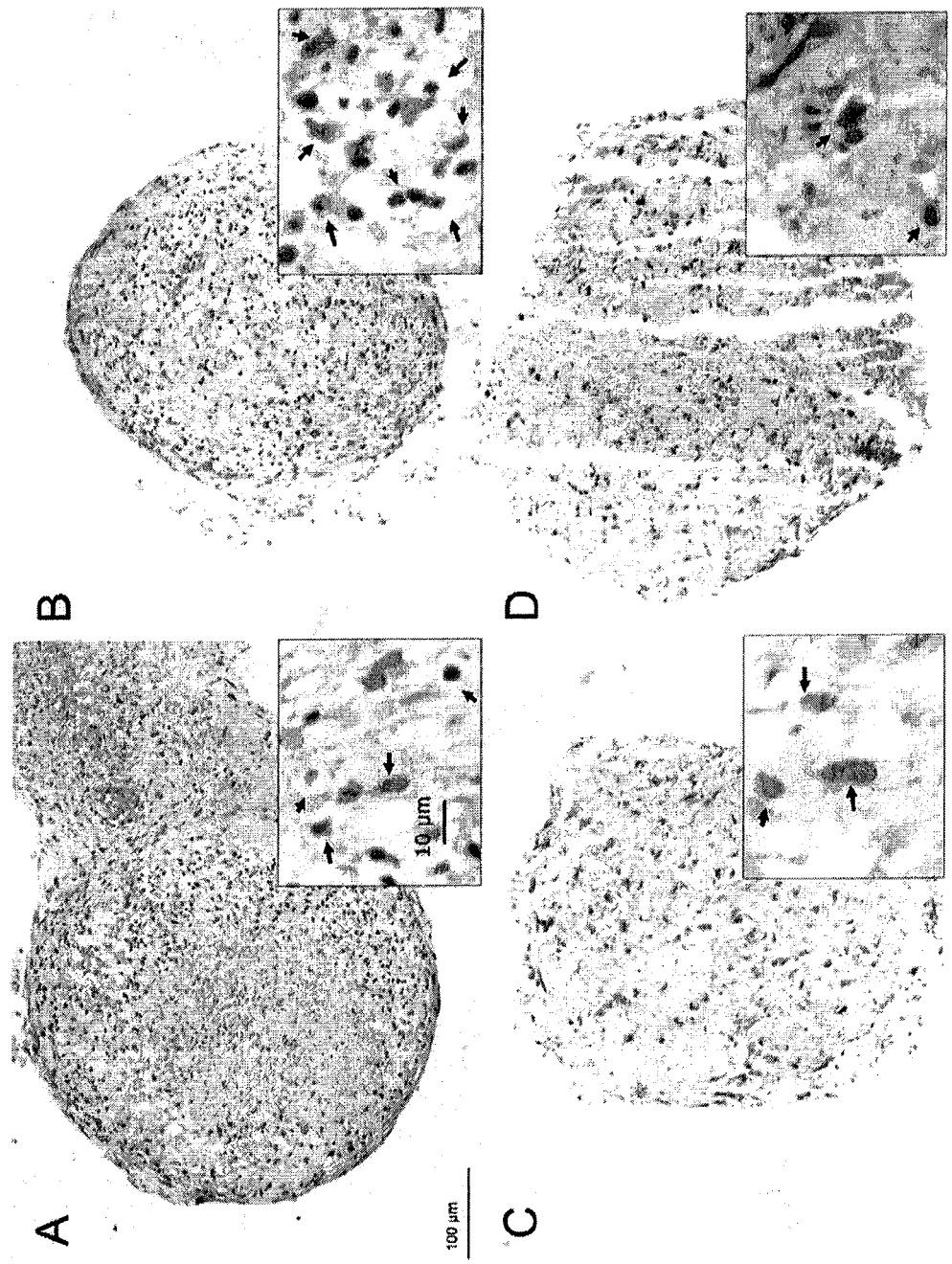

FIG. 4(A-D) illustrates the presence of chondrocyte phenotype (arrows) in paired (A, B) rat TDSCs and (C, D) rat BMSCs isolated from GFP rats after chondrogenic induction for (A, C) 14 and (B, D) 21 days. Stain: haematoxylin and eosin; Magnification: 200×; insert: 400× FIG. 4(E-H) illustrates the glycoaminoglycan deposition in paired (E, F) rat TDSCs and (G, H) rat BMSCs isolated from GFP rats after chondrogenic induction for (E, G) 14 and (F, H) 21 days. Stain: alcian blue; Magnification: 200×; insert: 400×; FIG. 4(I-K) illustrates the ratio of mRNA expression of (I) Col2A1, (J) Acan, (K) Sox9 in basal medium or chondrogenic medium in paired rat TDSCs and rat BMSCs isolated from GFP rats at day 0, 7, 14 and 21. *p≤0.050

More chondrocyte-like cells were observed in the cell pellets formed by rat TDSCs at both day 14 and day 21. There was more glycoaminoglycan deposition in the cell pellets formed by rat TDSCs compared to the cell pellets formed by rat BMSCs at both day 14 and day 21. There was significantly higher expression ratios of Col2A1 and Acan but not Sox9 in rat TDSCs compared to rat BMSCs upon chondrogenic induction.

Figure 5:
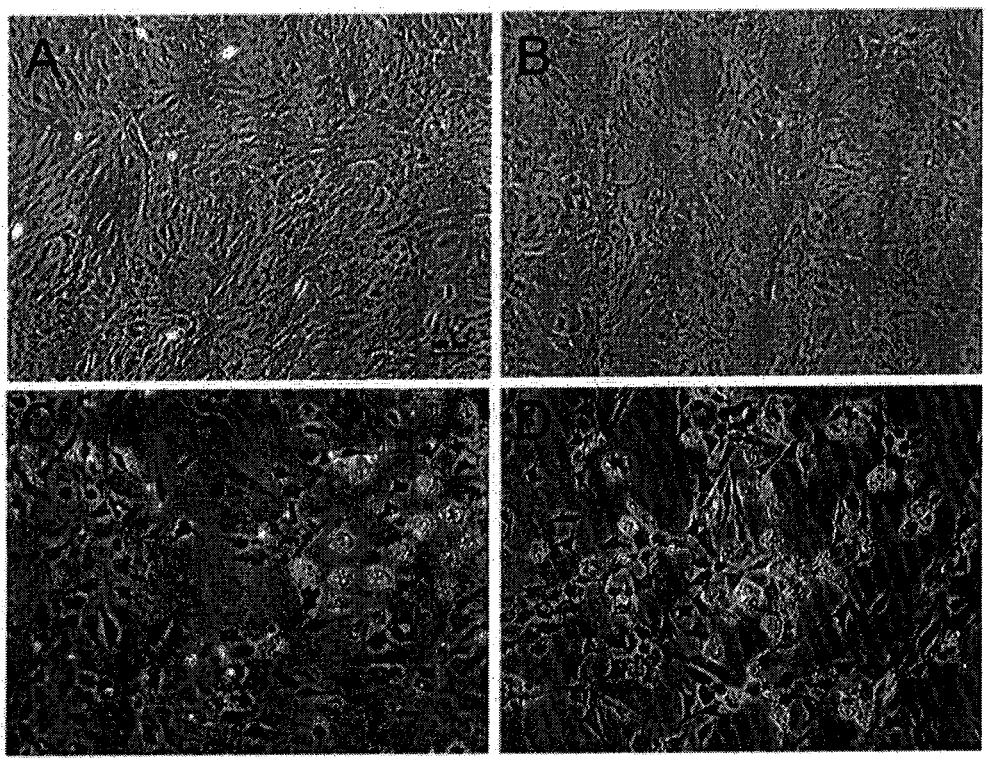

FIG. 5(A-D) illustrates the Oil Red 0 staining of oil droplets in paired (A, C) rat BMSCs and (B, D) rat TDSCs isolated from GFP rats in (A, B) basal or (C, D) adipogenic induction media for 21 days. Magnification: 100×. Scale bar=100 μm; FIG. 5(E-F) illustrates the mRNA expression of (E) PPARγ2 and (F) C/EBPα in paired rat TDSCs and rat BMSCs isolated from GFP rats in basal medium or adipogenic medium for 21 days. *p≤0.050

More oil droplets were formed in rat TDSCs compared to rat BMSCs upon adipogenic induction for 21 days. There was significantly higher expression of PPARγ2 (p=0.006), but not C/EBPα (p=0.262) in rat TDSCs compared to rat BMSCs upon adipogenic induction.

Figure 6:
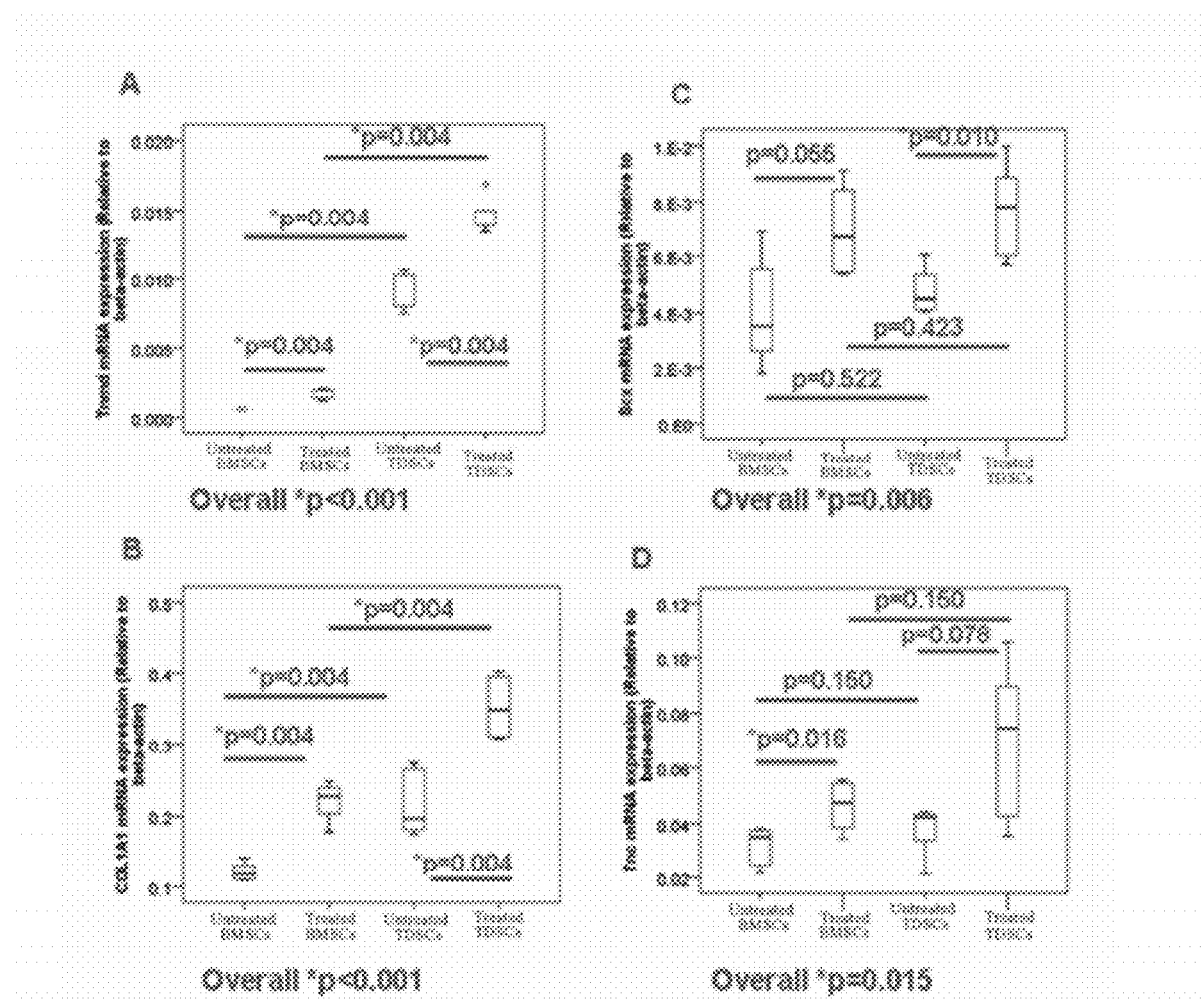

FIG. 6 illustrates the mRNA expression of tendon-related markers in paired rat TDSCs and rat BMSCs isolated from GFP rats after tenogenic induction. (A) tenomodulin (Tnmd); (B) collagen type I alpha 1 (Col1A1); (C) scleraxis (Scx) and (D) tenascin C (Tnc). *p≤0.050

Rat TDSCs showed higher expression of Tnmd (p=0.004) and Col1A1 (p=0.004), but not Scx (p=0.423) and Tnc (p=0.150), compared to rat BMSCs, in basal medium and upon induction.

Figure 7:
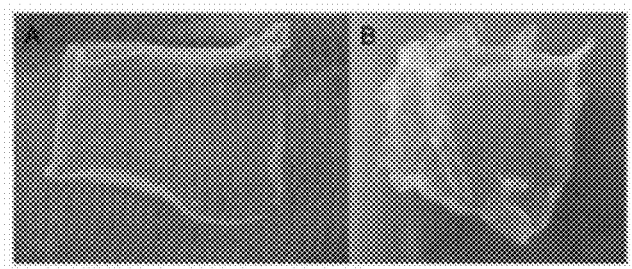

FIG. 7 illustrates the gross view of (A) rat TDSC sheet and (B) human TDSC sheet formed by TDSCs isolated from GFP rat and human TDSCs isolated from hamstring tendon, respectively and treated with CTGF and ascorbic acid. After treatment of rat and human TDSCs with CTGF and ascorbic acid for 2 weeks and 4 weeks, respectively, abundant extracellular matrix was produced and cellular sheets were formed. The TDSC sheets could not be easily digested by trypsin.

Figure 8:
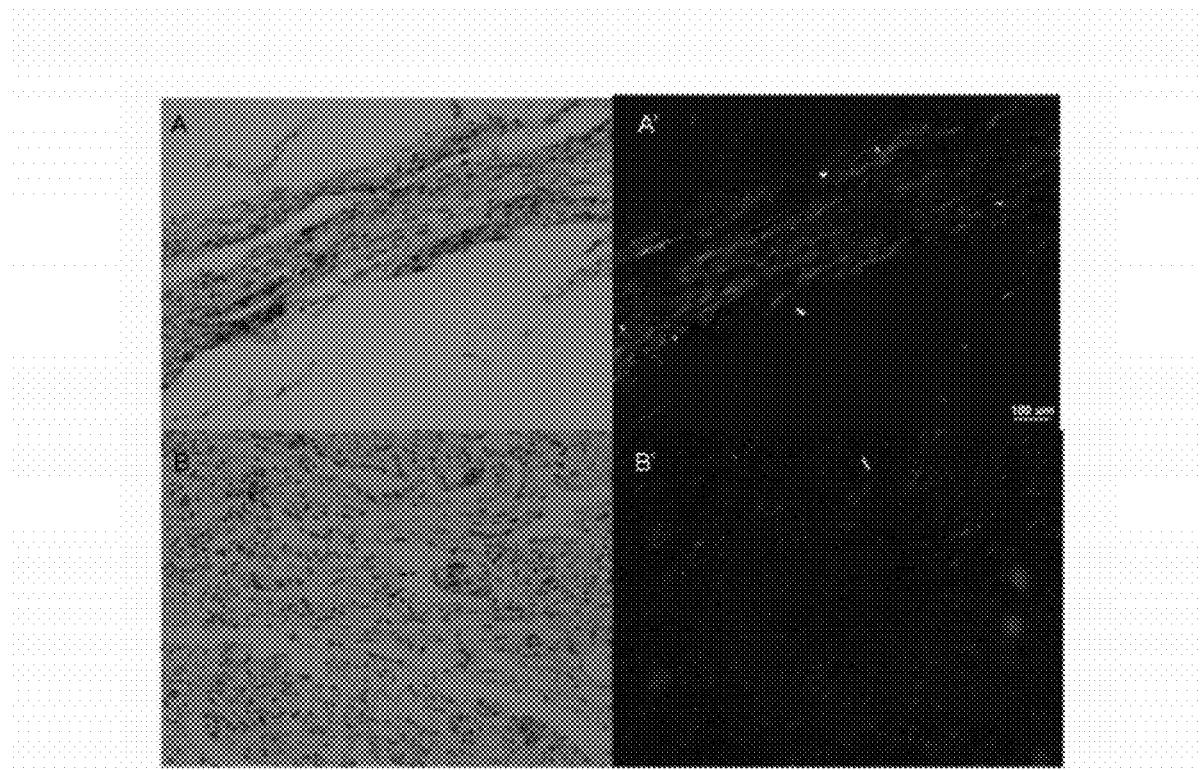
Figure 9:
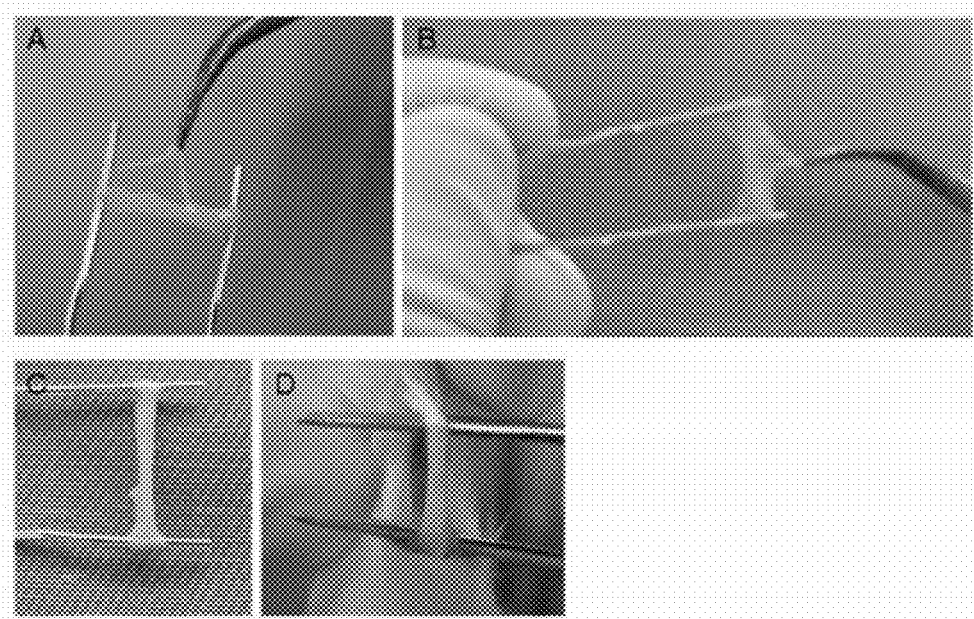

FIG. 8(A-B, A'-B') illustrates the histology of the cell sheet formed by (A, A') rat TDSCs and (B, B') rat BMSCs isolated from GFP rats upon treatment with CTGF and ascorbic acid. The cellularity was high. The stem cells were round and randomly oriented in the extracelluar matrix. More extracellular matrices were produced in rat TDSCs (A) compared to rat BMSCs (B). Polarization microscopy also confirmed that the collagen fibrils were thin and randomly oriented. More longitudinally-aligned fibrils were observed in rat TDSCs (A') compared to rat BMSCs (B'). Stain: Haematoxylin and eosin; Magnification: 100×; scale bar=100 μm FIG. 9(A-C) illustrates the formation of a bio-artificial tendon and ligament after rolling the cell sheet formed by treated rat TDSCs isolated from GFP rats and loading it on an U-shaped spring. FIG. 9(D) shows the intact rat flexor tendon for comparison.

Figure 10:
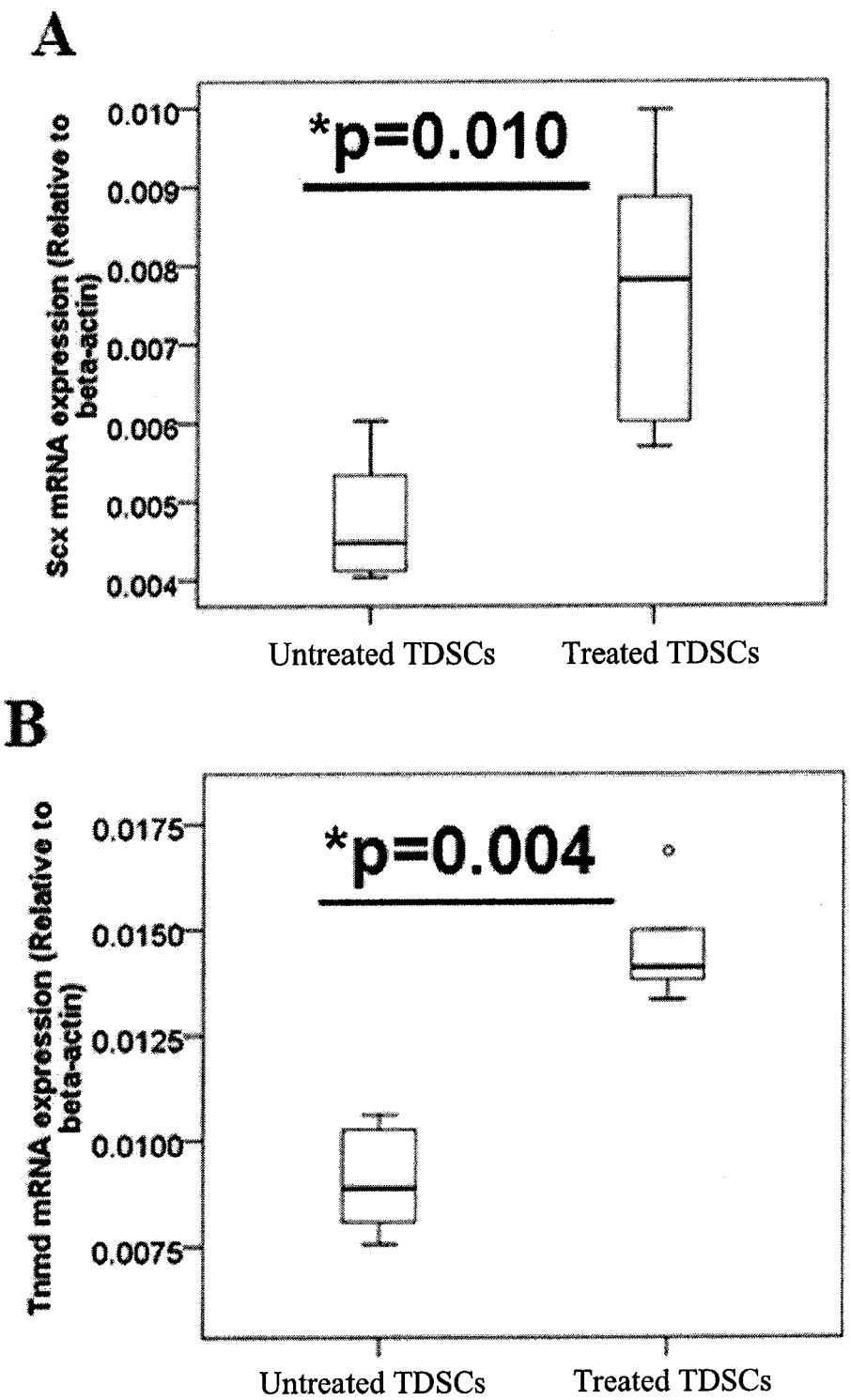

FIG. 10 illustrates the mRNA expression of tendon-related markers in rat TDSCs isolated from GFP rats after treating the cells with CTGF and ascorbic acid to induce the formation of the cell sheet. (A) scleraxis (Scx), (B) tenomodulin (Tnmd), (C) collagen type I alpha 1 (Col1A1) and (D) tenascin C (Tnc). *p≤0.050

The expression of Tnmd (p=0.004), Scx (p=0.010) and Col1A1 (p=0.004) increased in rat TDSCs after treatment. The increased in the expression of Tnc in rat TDSCs was not statistically significant (p=0.078).

FIG. 11 illustrates the mRNA expression of cartilage-(Col2A1, Acan) and bone-related (Bglap) markers of paired rat TDSCs and rat BMSCs isolated from GFP rats in the cell sheet. The expression of (A) Col2A1 (p=0.004 and p=0.037, respectively) and (C) Bglap (p=0.018 and p=0.025, respectively) decreased in both rat TDSCs and rat BMSCs after forming the cell sheet. The expression of (B) Acan decreased in rat TDSCs (p=0.004) but not in rat BMSCs (p=0.873) after forming the cell sheet. However, the expression of Col2A1 (p=0.004), Acan (p=0.004) and Bglap (p=0.006) remained higher in rat TDSCs compared to that in rat BMSCs after forming the cell sheet. *p≤0.050

FIG. 12 illustrates the (A-E) collagenase and (F-J) non-collagenous proteins production by rat TDSCs isolated from GFP rats after treatment with CTGF and ascorbic acid to induce the formation of the cell sheet using Sirius Red F3BA staining assay and Fast Green FCF staining assay, respectively. Untreated TDSCs: (A, C, F, H): Treated TDSCs: (B, G, D, I); magnification: (C, D, H, I): 100×

FIGS. 12(E) and (J) illustrates the absorbance of the Sirius Red F3BA and Fast Green FCF stains, respectively, in the treated and untreated TDSCs. *p≤0.050

There was higher expression of collagenous (p=0.004) and non-collagenous protein (p=0.006) production by the cells in the cell sheet.

FIG. 13 illustrates the (A) water content, (B) sulfated glycoaminoglycans (sGAG), and acetic acid-pepsin-soluble fraction of (C) total collagen, (D) collagen type I and (E) collagen type III of human TDSCs isolated from hamstring tendon after treatment with CTGF and ascorbic acid for 4 weeks to induce the formation of the cell sheet. Human hamstring tendon is used a reference.

The human TDSC sheet contained 90.2±1.4% of water and 18.0±1.6% (dry weight) of sGAG. The acetic acid-pepsin-soluble fraction contained 4.5±4.0% (dry weight) of total collagen, of which it was mainly collagen type I (5.4±4.8% dry weight). There was only small amount of collagen type III (8E-05±2.5E-05% dry weight) and the level of collagen type II was below the sensitivity limit of 2 ng/ml of the ELISA kit (results not shown).

FIG. 14(D) illustrates the synthesis and secretion of collagen fibrils into the extracellular space (arrows) by human TDSCs after treatment with CTGF and ascorbic acid for 4 weeks to form the cell sheet as observed under the scanning electron microscopy. The collagen fibrils were getting organized (E-F). FIG. 14(A-C) shows the organization of collagen fibrils in human hamstring tendon for references. Scale bar: 10 μm (A, D); 1 μm (B, C, E, F). The square in (D) is shown in (F). FIG. 14(G) showed the diameter of collagen fibrils in human hamstring tendon and human TDSC sheet as measured by image analysis software.

The collagen fibrils in the human TDSC sheet were small and not well-organized when compared to the collagen fibrils in intact human hamstring tendon. The collagen fibrils were produced inside the cells and secreted into the extracellular space in the treated human TDSCs (arrowhead). In some areas that were collagenized, the cell boundary became indistinct (arrow). There was uni-modal distribution of collagen fibrils in human TDSC sheet, similar to that in human hamstring tendon. The fibril size was 86.1±25.1 nm (range: 50 nm-200 nm) in the human TDSC sheet compared to 141.5±35.2 nm (range: 70 nm-250 nm) in the human hamstring tendon (p<0.001).

FIG. 15 illustrates the in vivo development and maturation of the cell sheet formed with green fluorescent protein (GFP)-TDSCs isolated from GFP rats in the nude mouse model. FIG. 15(A) shows the subcutaneous transplantation of the cell sheet. FIG. 15(B) illustrates the transplanted tissue at 8 weeks after transplantation.

FIG. 15(C-E, C'-E') shows the histology of the cell sheet before, at week 6 and week 8 after transplantation, respectively. The cellularity and vascularity (arrows) at week 6 after transplantation were high (D). The cells were still randomly-oriented and were round (D). There was mass extracellular matrix production (D) but not well-organized as indicated by polarized microscopy (D'). At week 8 after transplantation, the cellularity was reduced (E). Tendon- and ligament-like tissues were formed (E). The cells became spindle-shaped, longitudinally-arranged along the loading axis and were embedded between parallel fibrils (E). The fibrils were thicker at week 8 than that before transplantation and showed the typical collagen birefringence of tendon/ligament (E').

FIG. 15(F, F', G, G') shows the higher magnification of the cell sheet after transplantation in the nude mouse model for 6

(F, F') and 8 (G, G') weeks. The cells were longitudinally-aligened along the loading axis and embedded between the parallel collagen fibrils at week 8 (star, F).

Stain: Haematoxylin & eosin; Magnification: (C-E, C'-E'): 50×; (F, F', G, G'): 200×; scale bar=100 µm; arrows: blood vessels; star: aligned cells FIG. 15(H, I) shows the ex vivo fluorescent imaging of the cell sheet after transplantation in the nude mouse model for 6 (H) and 8 weeks. Green fluorescent signal could be detected because the TDSCs used for cell sheet formation was isolated from GFP rat. No fluorescent signal was observed at week 6 nude mouse transplanted with the cell sheet without loading. The cell sheet degraded and could not be found (left mouse of FIG. 15H). Fluorescent signal could be detected in the transplanted tissue sutured to the spinal muscle in the nude mouse at week 6 and week 8.

FIG. 16 illustrates the surgical procedure of suturing rat GFP-TDSC sheet into the rat patellar tendon window wound and the presence of the GFP-TDSCs in the window wound at week 2 by ex vivo fluorescent imaging. FIG. 16(A) illustrates the creation of a window wound in the patellar tendon with two stacked blades. FIG. 16(B & C) illustrates the rolling and suturing of the cell sheet to the patellar bone and proximal tibia in the window wound. FIG. 16(D, E) illustrates the injured patellar tendon without the cell sheet (D) and with the cell sheet (E) at week 2. FIG. 16(F) and (G) shows the corresponding fluorescent images of FIG. 16(D) and FIG. 16(E), respectively, at week 2.

Figure 17:
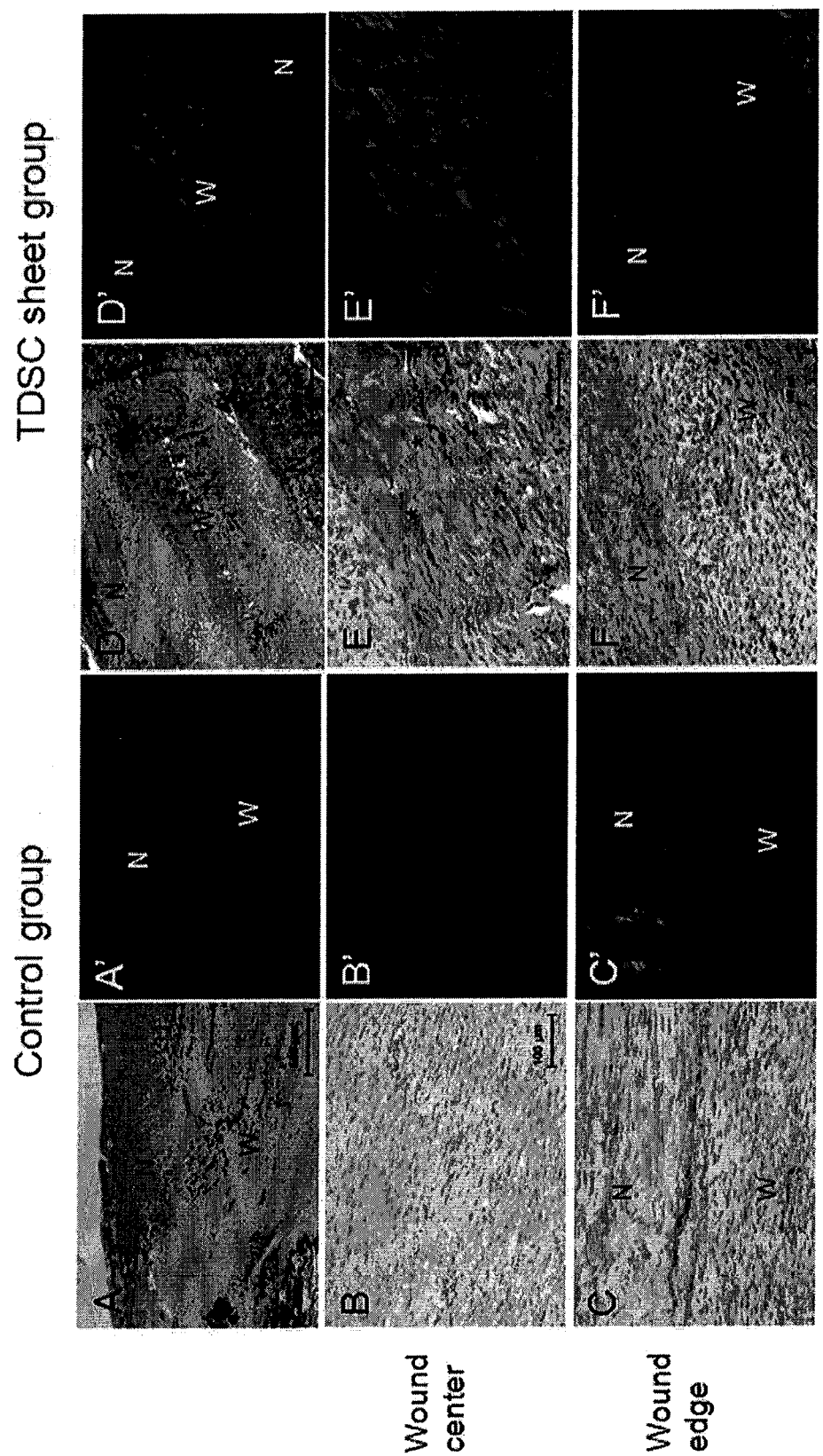

FIG. 17 illustrates the effect of the cell sheet formed with TDSCs isolated from GFP rats in the promotion of healing in a patellar tendon window injury rat model as shown by histology at week 2.

Figure 18:
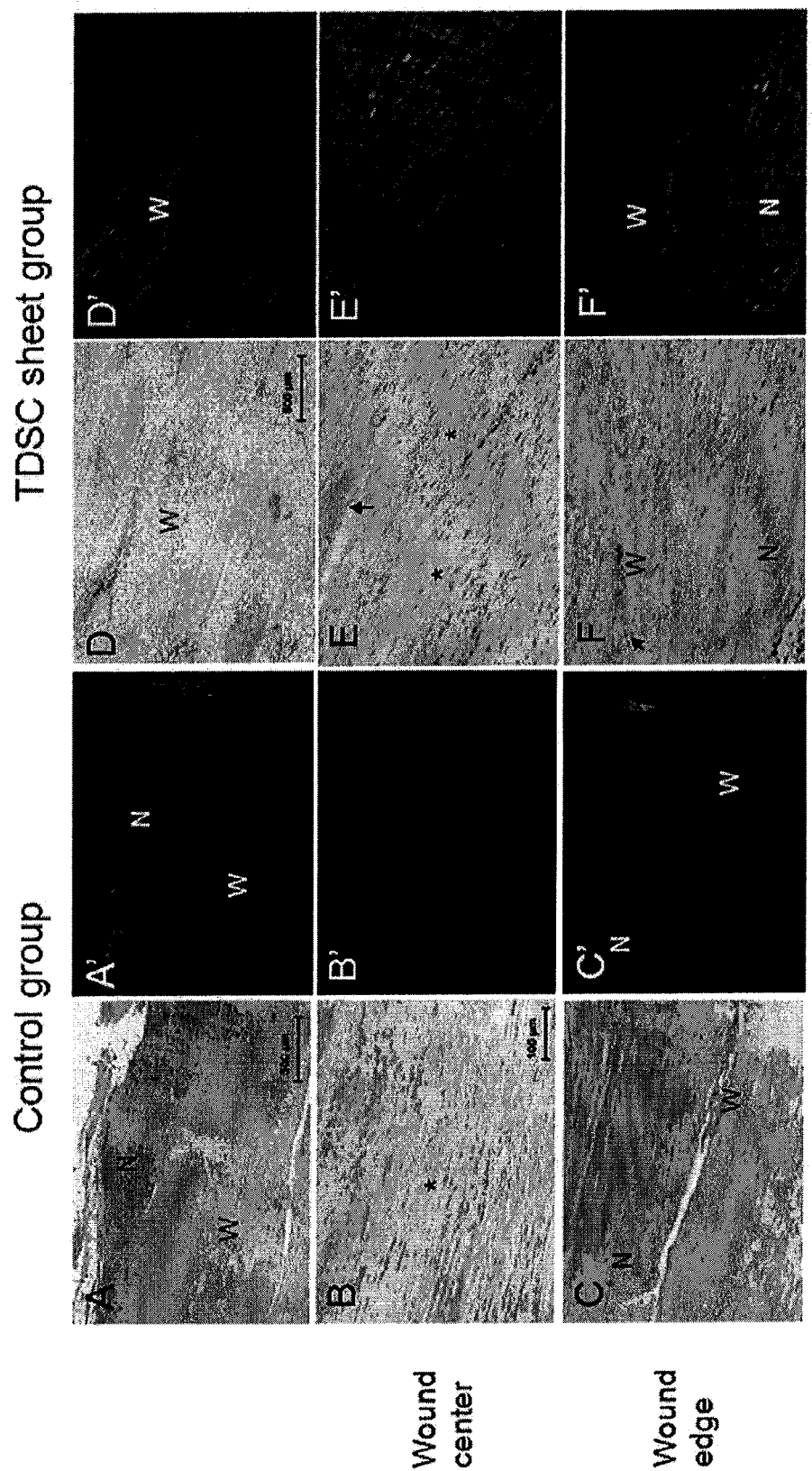

The cellularity seemed to be higher in the TDSC sheet group compared to that in the control group, possibly due to cell sheet transplantation (C versus F). Higher collagen expression as indicated by haematoxylin and eosin stability of the extracellular matrix was observed in the TDSC sheet group compared to that in the control group. Elongated fibroblast-like cells aligned between parallel collagen fibers were observed in the center of the window wound in the TDSC sheet group (*, E) but not in the control group (B). This was accompanied by higher collagen birefringence in the window wound in the TDSC sheet group (E') compared to that in the control group under polarization microscopy (B'). The wound boundary could be easily identified in both groups (C, E). Stain: Haematoxylin and eosin; A'-F' were the corresponding polarized images. Scale bar=500 µm (A, A', D, D'); Scale bar=100 µm (B, B', C, C', E, E', F, F'); Magnification: 50× (A, A', D, D'); 200× (B, B', C, C', E, E', F, F'); *: longitudinal alignment of fibroblast-like cells; N: normal intact tendon next to the window wound; W: wound area FIG. 18 illustrates the effect of the cell sheet formed with TDSCs isolated from GFP rats in the promotion of healing in a patellar tendon window injury rat model as shown by histology at week 8.

Figure 19:
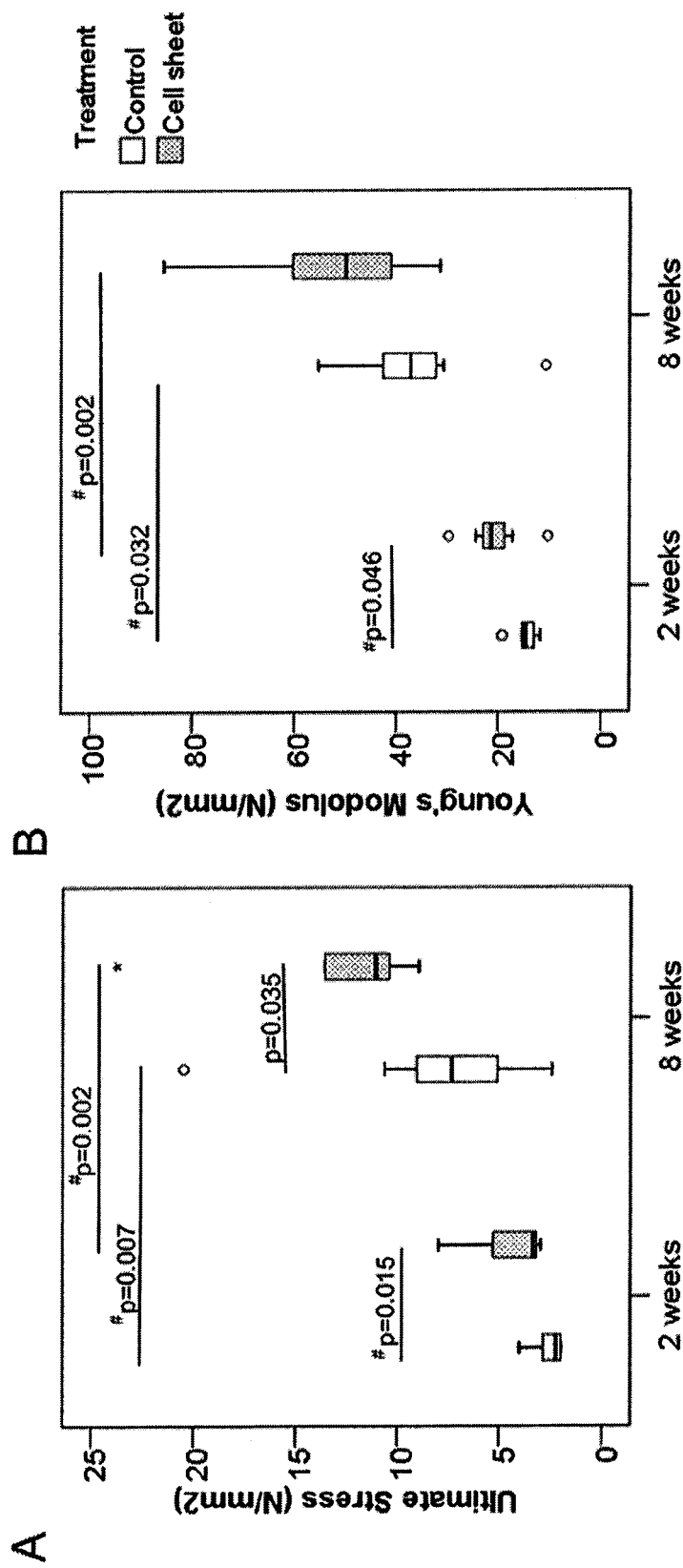

At week 8, the cellularity inside wound was reduced in both groups but it remained higher in the TDSC sheet group (E, F) compared to that in the control group (B, C). Despite this, the cells and the collagen fibers were better aligned with higher collagen birefringence in the TDSC sheet group compared that in the control group at both the wound center (B, B' versus E, E') and the wound edge (C, C' versus F, F'). The wound boundary was less distinctive in the TDSC sheet group (FIG. 18F) compared to that in the control group (C). Stain: Haematoxylin and eosin; A'-F' were the corresponding polarized images. Scale bar=500 µm (A, A', D, D'); Scale bar=100 µm (B, B', C, C', E, E', F, F'); Magnification: 50× (A, A', D, D'); 200× (B, B', C, C', E, E', F, F'); *: longitudinal alignment of fibroblast-like cells; arrow: blood vessel; N: normal intact tendon next to the window wound; W: wound area FIG. 19 illustrates the (A) ultimate stress and (B) Young's modulus of the regenerated tissue without and with transplantation of cell sheet formed by TDSCs isolated from GFP rats after transplantation into the patellar tendon window defect for 2 weeks and 8 weeks. #p≤0.050; "o" and "*" represent outliner and extreme value, respectively, in the study.

There was significant increase in the ultimate stress (p=0.002 for TDSC group and p=0.007 for control group) and Young's modulus (p=0.002 for TDSC group and p=0.032 for control group) of the regenerated tissue from week 2 to week 8 in both the TDSC sheet group and the control group. The ultimate stress at week 2 (p=0.015; 4.5±1.9 N/mm$^2$ versus 2.5±0.8 N/mm$^2$) and week 8 (p=0.035; 13.1±5.0 N/mm$^2$ versus 8.4±5.9 N/mm$^2$) (A) as well as the Young's modulus at week 2 (p=0.046; 20.7±6.0 N/mm$^2$ versus 14.9±2.5 N/mm$^2$) (B) were significantly higher in the TDSC sheet group compared to those in the control group. While the Young's modulus in the TDSC group was also higher than that in the control group at week 8, it did not reach statistical significance (p=0.110; 52.8±18.7 N/mm$^2$ versus 36.2±13.8 N/mm$^2$) (B).

DETAILED DESCRIPTIONS

The embodiments will be further described below with reference to the figures.

As used herein, the term "stem cell" refers to cell exhibiting self-renewal and multi-lineage differentiation potential. "Treated stem cell" refers to the stem cell which has been treated by biological, chemical, genetic, biomechanical or biophysical factors, leading to the production of the biological factors by the stem cell or maturation of the cell sheet as disclosed herein.

As used herein, the term "biological factors" refer to all proteins made of amino acids that can modulate the biological activities of a cell.

In one aspect disclosed herein, a cell sheet is formed using a stem cell for the promotion of tissue repair and bio-artificial tissue engineering.

In an embodiment, the cell sheet as disclosed herein is prepared by a method comprising treating stem cells so that the treated stem cells can be embedded in their self-secreted extracellular matrix (ECM) and forming a cell sheet. Accordingly, the cell sheet disclosed herein comprises treated stem cells and self-secreted extracellular matrix thereof in which the treated stem cells are embedded.

Chemical, biological, genetic, biomechanical or biophysical factors or agents for formation of the cell sheet of this invention such as, but not limited to, compounds such as growth factors, chemical agents or biomaterials; or genetic modification, in vitro mechanical loading or biophysical intervention of the stem cell can be used for the stem cell or the cell sheet of this invention if they modulate the degree and activity of the cell or the cell sheet.

In another embodiment, the cell sheet as disclosed herein comprises about 50-95% w/w water, and therefore the dry weight of the cell sheet is about 5-50% w/w based on the total weight of the sheet. The cell sheet can comprise compounds selected from the group consisting of collagen selected from the group consisting of Collagen type I, Collagen type III, Collagen type II, or any combination thereof; proteoglycan selected from the group consisting of aggrecan, decorin, biglycan or a any combination thereof; and glycoprotein selected from the group consisting of elastin, cartilage oligomeric matrix protein (COMP), tenascin C or any combination thereof; or any combination thereof.

In still another embodiment, the cell sheet comprises collagen: 40-90% w/w; Proteoglycan: 0.5-30% w/w; and Glycoprotein of 1-30% w/w based on dry weight of the sheet. In another preferable embodiment, the collagen comprises Collagen type I: 70-98% w/w, Collagen type III: 1-15% w/w, and Collagen type II: 1-5% based on the total weight of the collagen; further preferably comprise Collagen type I: 70-98% w/w Collagen type III: 1-5% w/w, and Collagen type II: 1-5% based on the total weight of the collagens.

In still another embodiment, the cell sheet disclosed herein comprises fibrils of diameter of 5-500 nm. Preferably, the cell sheet has fibrils of diameter of 50-250 nm. The cell sheet has ultimate stress of at least 1 N/mm$^2$, more preferably, at least 5 N/mm$^2$, still more preferably about 5-10 N/mm$^2$ The value of the stress depends on the culturing conditions, but is based on the current setting. For example, the rat TDSC sheet after culturing with CTGF and ascorbic acid for 2 weeks and after folding, can reach about 5-10N/mm$^2$ during load to failure.

In alternative embodiment, the stem cell used in the invention is an adult stem cell. The stem cell is isolated from animal or human tissues. The stem cell used for the production of the cell sheet is autologous or allogeneous. The stem cell of the invention can be isolated from, but not limited to, tendon and ligament tissue, bone morrow, adipose tissue or dental pulp. In an embodiment, stem cell that proliferates fast, shows high colony-forming ability, and exhibits high expression of target tissue-specific markers and produces high level of ECM has the advantage of forming the cell sheet as a result of shortening the in vitro cell culture time and increasing the success of forming the cell sheet in vitro upon treatment. In a preferred embodiment, the stem cell is tendon-derived stem cell (TDSC). TDSC is stem cell isolated from tendon according to Rui et al. Tissue Eng Part A 2010; 16(5): 1549-1558. The cell forms colonies, exhibits higher cell proliferation at low cell density, expresses surface markers CD44 and CD90 but is negative for the surface markers CD31 and CD34. The cell further exhibits multi-lineage differentiation potential and differentiates into tendon, ligament, cartilage (chondrocyte) or osteoblast upon induction. Referring to FIGS. 1-6, TDSC exhibits higher colongenicity, proliferative potential and multi-lineage differentiation potential, both at basal level and upon induction, compared to bone marrow-derived stem cell (BMSC). TDSC therefore is good stem cell source for cell sheet formation.

Allogeneic or autologous TDSC is readily available from the waste material of tendon/ligament surgery such as the tendon graft tissue in ACL reconstruction and the tendon and ligament tissue in total knee replacement. The isolation of stem cell from waste tissue in routine surgery has the advantage of avoiding additional pain to patients compared to the isolation of BMSC by bone marrow aspiration and the isolation of adipose tissue-derived stem cells (ADSC) by liposuction. The allogeneic stem cell is used immediately after isolation or kept in liquid nitrogen until needed for producing the cell sheet.

Other aspect disclosed herein is to provide a method of producing the cell sheet as disclosed herein. The method comprises the steps of treating stem cells with biological factors or factors leading to a maturation of the cell sheet and/or a production of biological factors including the biological factors used for the treatment, whereby inducing a differentiation of the stem cells, a production of ECM and hence formation of a cell sheet in vitro.

In embodiments disclosed herein, the biological factors used in the invention are proteins made of amino acids that can modulate the biological activities of a cell. In an embodiment, the biological factors comprise the Transforming Growth Factor family (TGF) such as TGF-β, together with ascorbic acid. In another embodiment, the biological factors comprise the Growth Differentiation Factor/Bone Morphogenetic Protein (GDF/BMP) family members such a GDF-5/BMP-14, GDF-6/BMP-13 and GDF-7/BMP-12, together with ascorbic acid. In a preferred embodiment, the biological factors used to induce the formation of the cell sheet are Connective Tissue Growth Factor (CTGF) and ascorbic acid.

In other embodiments, the factors leading to the production of the biological factors of the invention or maturation of the cell sheet can further be chemical, genetic, biomechanical or biophysical factors or agents.

In still alternative embodiments, the method of the invention comprises use of chemical and biological agents to induce production of the biological factors, and/or use of genetic modification to induce the overexpression of the biological factors. In an alternative embodiment for formation of the cell sheet, in vitro mechanical loading or biophysical modalities can be additionally used to the cell or cell sheet. In another alternative embodiment for formation of cartilage, compression is applied to the cell or cell sheet as a mechanical force to stimulate the formation of cartilage. In still another alternative embodiment for formation of bone, muscle, tendon or ligament, tensile as a mechanical force is applied to the cell or cell sheet to form bone-, muscle-, tendon- or ligament-like tissues.

In another alterative embodiment for using the resulting cell sheet for cartilage repair, compressive load is applied to the cell or cell sheet as a mechanical force to stimulate the formation of cartilagous matrix. In still another alternative embodiment for bone, muscle, tendon or ligament healing, tensile as a mechanical force is applied to the cell or cell sheet to stimulate the bone-, muslce-, tendon- or ligament-like extracellular matrix.

In other embodiments, the cell sheet is further chemically, biologically, genetically, biomechanically and/or biophysically modified and/or added with biomaterials such that the modification modulates the degree and activity of the cell or the cell sheet.

In one embodiment of the method of producing the cell sheet, the stem cell is isolated from tissue and banked in liquid nitrogen if required. When required to form the cell sheet, the stem cell is thawed from liquid nitrogen. The cell is seeded, expanded in culture dish and grown until confluence. Afterwards, the cell is treated with biological factors in culture medium. Culture medium with the biological factors in culture is changed regularly until the formation of the cell sheet.

Another aspect disclosed herein is to provide use of the cell sheet as disclosed herein, optionally with an active stem cell, for enhancing tissue repair. In one embodiment, it is provided use for the repair of window injury in the patellar tendon. The window injury of the patellar tendon is caused by removal of the patellar bone-patellar tendon-bone graft in anterior cruciate ligament (ACL) reconstruction. In the embodiments of the invention, the cell sheet is used in a method enhancing the repair of window injury in the patellar tendon comprising the steps of rolling and suturing the cell sheet in the window defect. The cell sheet of the invention can be used to enhance suture repair of tendon (e.g. Achilles tendon, hand tendon) and ligament (e.g. posterior cruciate ligament, PCL; ACL) by wrapping the cell sheet around the rupture site.

In yet another embodiment, the cell sheet of the invention is used to promote tendon-bone junction regeneration in ACL reconstruction. Accordingly, the cell sheet is used in a method of promoting tendon-bone junction regeneration in ACL reconstruction comprising the steps of wrapping the tendon graft with the cell sheet, similar to the use of periosteal autograft by other groups (Ohtera et al., Crit Rev Biomed Eng 2000; 28(1-2): 115-118; Youn et al., Clin Orthop Relat Res 2004; 419: 223-231; Chen et al., J Orthop Surg Taiwan 2003; 20: 21-29). In another embodiment, the cell sheet is used for rotator cuff repair by suturing the cell sheet to the interface between tendon and bone.

In yet another embodiment, the cell sheet is used for the repair of bone fracture, osteoarthritis, osteo-chondro defect, muscle tear, skin wound or burn by putting the cell sheet in the defect.

In alternative embodiments, it is to provide use of the acellular product of the cell sheet alone or in combination with other cell types or growth factors for the promotion of tissue repair. The cell sheet is used as an acellular biomaterial for tissue engineering application similar to the above after decellularization. When used alone, it is used to prevent repair gap formation or failure, enhance host cell attachment, infiltration and proliferation. The cell sheet as a decellularized product can be used together with other known growth factors and cell types for the promotion of tissue repair.

Another aspect disclosed herein relates to use of the cell sheet disclosed herein to form a bio-artificial organ for tissue replacement. The cell sheet, together with biomaterials, chemical, biological, biomechanical, biophysical factors in vitro and/or in vivo maturation in an animal, preferably in an immunodeficient animal such as a nude mouse, or an animal, to which the stem cell is autologous, forms a bio-artificial organ for tissue replacement.

Still another aspect disclosed herein relates to a method for the repair of bone fracture, osteoarthritis, osteo-chondro defect, muscle tear, skin wound or burn, comprising the steps of putting the cell sheet in the defect.

EXAMPLES

Example 1

Preparation of Cell Sheet

The stem cells of rat TDSC were isolated from a rat tendon according to Rui et al. Tissue Eng Part A 2010; 16(5): 1549-1558. The isolated TDSC was frozen in liquid nitrogen until use. In order to form the cell sheet, TDSC was expanded in plastic culture dish in growth medium until confluence. It was then treated with CTGF (5 ng/ml-1 µg/ml) and ascorbic acid (5-100 µM) in low glucose Dulbeco's Modified Eagle Medium (LG-DMEM) (Gibco), 2-30% fetal bovine serum (FBS), 10-500 U/ml penicillin, 10-500 µg/ml streptomycin and 1-10 mM L-glutamine at 10-45° C., 3-10% $CO_2$ in a humidified cell culture chamber for 1-6 weeks. Medium with CTGF and ascorbic acid was changed every 2-5 days. Referring to FIG. 7 and FIG. 12, the treated cell differentiated, produced abundant extracellular matrix and the cell sheet thus formed was elastic after treating the stem cell with ascorbic acid (25 µM) and CTGF (25 ng/ml) in DMEM at 2% FBS at 37° C., 5% $CO_2$ in a humidified chamber. Medium with CTGF and ascorbic acid was changed every 3 days. Referring to FIG. 8 and FIG. 14, histology and scanning electron microscopy showed that the cell embedded in the self-secreted ECM is still round and randomly-oriented. Thin collagen fibrils were seen at week 2 in the cell sheet formed with rat TDSCs in histology and at week 4 in the cell sheet formed with human TDSCs in scanning electron microscopy.

Referring to FIG. 8, better cell sheet was formed with TDSC compared to BMSC isolated from rat tendons, with more ECM and longitudinally-aligned fibrils in this condition. Referring to FIG. 10 and FIG. 11, treatment of rat TDSC with CTGF and ascorbic acid promoted differentiation of the cell towards tenogenic lineage as indicated by the increased mRNA expression of Tnmd, Scx and Col1A1 while the mRNA expression of cartilage-(Col2A1, Acan) and bone-related (Bglap) markers decreased. This is consistent with the differentiation of the stem cell upon treatment during formation of the cell sheet. However, as the mRNA expression of chondrocyte-(Col2A1, Acan) and bone-related (Bglap) markers remained high after treatment, compared to those in BMSC, the cell sheet thus formed by treating TDSC with CTGF and ascorbic acid is still good for other tissue repair such as, but not limited to, bone, tendon-bone junction, cartilage, skin and muscle repair.

Referring to FIG. 7B and FIG. 14, in another experiment, human TDSC were isolated from a waste tendon according to Rui et al. Tissue Eng Part A 2010; 16(5): 1549-1558, and illustrated similar properties to the rat TDSC as shown above.

According to FIG. 13, the human TDSC sheet formed after treatment with CTGF and ascorbic acid for 4 weeks contained 90.2±1.4% of water and 18.0±1.6% (dry weight) of sGAG. The acetic acid-pepsin-soluble fraction contained 4.5±4.0% (dry weight) of total collagen, of which it was mainly collagen type I (5.4±4.8% dry weight). There was only small amount of collagen type III (8E-05±2.5E-05% dry weight) and the level of collagen type II was below the sensitivity limit of 2 ng/ml of the ELISA kit.

According to FIG. 14, the human TDSC sheet formed after treatment with CTGF and ascorbic acid for 4 weeks synthesized and secreted the synthesized collagen fibrils into the extracellular matrix. The synthesized collagen fibrils of human TDSC sheet were less organized and smaller compared to the collagen fibrils of normal human hamstring tendon (Mean fiber diameter: 86.1 nm±25.1 nm versus 141.5±35.5 nm).

Example 2

Formation of a Bio-Artificial Tendon and Ligament

Referring to FIG. 9, the cell sheet formed with rat TDSC was rolled up and loaded on a U-shaped spring to form a bio-artificial tendon and ligament. Referring to FIG. 15, the cell sheet formed with rat TDSC matured further after transplantation and suturing to the spinal muscle. At week 8 after transplantation, the cellularity was reduced compared to that at week 6 and tendon- and ligament-like tissue was formed. The transplanted cells are alive, spindle-shaped, longitudinally-arranged along the loading axis and are embedded between the parallel fibrils. The fibrils were thicker than that before transplantation and show the typical collagen birefringence of tendon and ligament at week 8.

Example 3

Tissue Repair

The cell sheet, with the active TDSC, was used for enhancing the repair of window injury in the patellar tendon after removal of the patellar bone-patellar tendon-bone graft in anterior cruciate ligament (ACL) reconstruction by rolling and suturing the cell sheet in the window defect. Referring to FIGS. 16-19, suturing of the cell sheet formed with treated rat TDSC, to the patellar window defect promoted tendon healing. Some cells in the defect transplanted with the cell sheet were flattened at week 2. This was not observed in the group without the cell sheet. More ECM was observed in the group transplanted with the cell sheet. The ECM was longitudinally-arranged along the tendon and displays typical collagen birefringence of tendon and ligament. The transplanted cell sheet remained in the window defect at week 2 as shown by ex vivo fluorescent imaging. At week 8, the cells and the collagen fibers inside wound were better aligned with higher collagen birefringence in the TDSC sheet group compared that in the control group at both the wound center and the wound edge. The wound boundary was less distinctive in the TDSC sheet group compared to that in the control group. There was higher ultimate stress and Young's modulus in the TDSC sheet group compared to that in the control group at both week 2 and week 8. The differences reached statistical significance except Young's modulus at week 8.

Example 4

Suture Repair of Tendon

The cell sheet of the invention can be used to enhance suture repair of tendon (e.g. Achilles tendon, hand tendon) and ligament (e.g. posterior cruciate ligament, PCL; ACL) by wrapping the cell sheet around the rupture site.

Referring to FIGS. 10 and 15, the cell sheet formed by TDSC displays high tenogenic and ligmentogenic activity and was suitable for tendon and ligament repair.

Example 5

Repair of Bone Bracture, Osteoarthritis, Osteo-Chondro Defect, Muscle Tear, Skin Wound or Burn Referring to FIGS. 10 and 11, the cell sheet formed by TDSC expressed high level of tenogenic, chondrogenic and osteoblastic markers after treatment with CTGF and ascorbic acid for 2 weeks. This indicates that the cell sheet of the present invention can be used in repair of bone fracture, osteoarthritis, osteo-chondro defect, muscle tear, skin wound or burn.

The cell sheet disclosed herein (1) may eliminate the need to use scaffolds for stem cell delivery and hence alleviates problems of biocompatibility, biodegradability and immunogenicity that are commonly associated with synthetic scaffolds. (2) Both the presence of a natural ECM composition and preliminary fibrillar structure which provides contact guidance of tissue regeneration would provide the necessary in vivo-like environmental cues best suited for the survival, proliferation and differentiation as well as stimulate the regenerative responses of the stem cells. This is unparalleled by synthetic and natural scaffolds that contain only 1-2 matrix components. Problem with the transport of oxygen and nutrient, as with synthetic scaffolds, for the survival of stem cells is limited. (3) The cell sheet facilitates in vivo cell transplantation and provides some tensile mechanical strength for bearing early mechanical load (e.g. rehabilitation) during tissue repair. It will allow earlier rehabilitation for the promotion of earlier recovery after injury. (4) Referring to FIGS. 16-19, the cell sheet promotes tissue healing with earlier recovery and better healing quality and referring to FIG. 15, a tendon- and ligament-like tissue is formed.

The above descriptions of the embodiments are merely exemplary in nature and thus, variations thereof are not to be regarded as a departure from the spirit and scope of the invention.

The invention claimed is:

1. A cell sheet comprising:
   tendon-derived stem cells which have been treated with connective tissue growth factor (CTGF) and ascorbic acid, and
   extracellular matrix (ECM) secreted by the tendon-derived stem cells,
   wherein the tendon-derived stem cells are embedded in the ECM.

2. The cell sheet according to claim 1, wherein the cell sheet comprises compounds selected from the group consisting of collagen, proteoglycan, glycoprotein, and combinations thereof.

3. The cell sheet according to claim 2, wherein the collagen is selected from the group consisting of Collagen type I, Collagen type III, Collagen type II, and combinations thereof; the proteoglycan (PG) is selected from the group consisting of aggrecan, decorin, biglycan, and combinations thereof; and the glycoprotein is selected from the group consisting of elastin, cartilage oligomeric matrix protein (COMP), tenascin C, and combinations thereof.

4. The cell sheet according to claim 3, wherein the collagen comprises Collagen type I at 70-98% w/w, Collagen type III at 1-15% w/w, and Collagen type II at 1-5% w/w based on the total weight of the collagen.

5. The cell sheet according to claim 2 comprising collagen at 40-90% w/w; PG at 0.5-30% w/w; and glycoprotein at 1-30% w/w based on dry weight of the sheet.

6. The cell sheet according to claim 1, wherein the cell sheet comprises collagen, proteoglycan, and glycoprotein.

7. The cell sheet according to claim 1, wherein the stem cell is isolated from animal or human tissues.

8. The cell sheet according to claim 1, wherein the stem cells are autologous or allogeneic.

9. The cell sheet according to claim 1, wherein the cell sheet is further chemically, biologically, genetically, biomechanically and/or biophysically modified, and/or added with biomaterials.

10. The cell sheet according to claim 1, wherein the cell sheet comprises collagen fibrils of 5-500 nm in diameter.

11. The cell sheet according to claim 1, wherein the cell sheet has an ultimate stress of 1-10 N/mm$^2$.

12. A method for repairing tissue of a subject in need of tissue repair comprising applying the cell sheet according to claim 1 to a position on the subject where the tissue repair is required.

13. The method according to claim 12, wherein the tissue in need of repair is selected from the group consisting of tendon and ligament, bone, cartilage, muscle, and skin.

14. The method according to claim 13, wherein the tendon and ligament condition or disease is window injury of the patellar tendon after removal of the patellar bone-patellar tendon-bone graft in anterior cruciate ligament (ACL) reconstruction, tendon rupture, ligament rupture, rotator cuff injury or tendinopathy.

15. The method according to claim 13, wherein the bone in need of said repair is fractured.

16. The method according to claim 13, wherein the cartilage in need of said repair results from osteoarthritis or has osteo-chondro defect.

17. The method according to claim 13, wherein the muscle in need of said repair contains muscle tear.

18. The method according to claim 13, wherein the skin in need of said repair is wounded or burned.

19. A method for producing the cell sheet according to claim 1, comprising:

(a) collecting tendon-derived stem cells from fresh tissue or thawing previously frozen stem cells stored in liquid nitrogen;
(b) culturing the stem cells until confluence;
(c) treating the stem cells with connective tissue growth factor (CTGF) and ascorbic acid to induce differentiation of the stem cells, production of extracellular matrix and formation of a cell sheet in vitro.

* * * * *